United States Patent
de Sauvage et al.

(10) Patent No.: US 9,321,823 B2
(45) Date of Patent: Apr. 26, 2016

(54) MUTANT SMOOTHENED AND METHODS OF USING THE SAME

(75) Inventors: Frederic J. de Sauvage, Foster City, CA (US); Gerrit J.P. Dijkgraaf, San Francisco, CA (US); Thomas Januario, San Francisco, CA (US); Robert L. Yauch, Redwood City, CA (US)

(73) Assignees: Genentech, Inc., South San Francisco, CA (US); Curis, Inc., Lexington, MA (US)

( * ) Notice: Subject to any disclaimer, the term of this patent is extended or adjusted under 35 U.S.C. 154(b) by 865 days.

(21) Appl. No.: 13/394,069

(22) PCT Filed: Sep. 2, 2010

(86) PCT No.: PCT/US2010/047739
§ 371 (c)(1),
(2), (4) Date: Jul. 25, 2012

(87) PCT Pub. No.: WO2011/028950
PCT Pub. Date: Mar. 10, 2011

(65) Prior Publication Data
US 2012/0282259 A1 Nov. 8, 2012

Related U.S. Application Data

(60) Provisional application No. 61/239,364, filed on Sep. 2, 2009.

(51) Int. Cl.
C07K 14/705 (2006.01)
C07K 16/28 (2006.01)

(52) U.S. Cl.
CPC .................................. *C07K 14/705* (2013.01)

(58) Field of Classification Search
None
See application file for complete search history.

(56) References Cited

U.S. PATENT DOCUMENTS

| | | | |
|---|---|---|---|
| 5,990,281 A | 11/1999 | de Sauvage et al. | |
| 6,136,958 A * | 10/2000 | de Sauvage et al. | 530/388.22 |
| 6,407,216 B1 | 6/2002 | de Sauvage et al. | |
| 6,492,139 B1 | 12/2002 | de Sauvage et al. | |

FOREIGN PATENT DOCUMENTS

WO  WO-2007/059157 A1  5/2007
WO  WO 2012/047968 A2  4/2012

OTHER PUBLICATIONS

Ingham et al, Current Biology, 2000, 10:1315-1318, supplemental p. S1.*
Reifenberger et al (Cancer Research, 1998, 58:1798-1803).*
Dierks et al (Nature Medicine, 2007, 13:944-951).*
Santa Cruz Biotechnology (2015; SMO (H-300): Sc-13943).*
Chen et al (Genes and Development, 2002, 16:2743-2748).*
Xie et al. (Nature, 1998, 391:90-92).*
Chang, J., et al., "A Genomic Strategy to Elucidate Modules of Oncogenic Pathway Signaling Networks," Mol. Cell, 34(1):104-114 (2009).
Chen, J., et al., "Inhibition of Hedgehog Signaling by Direct Binding of Cyclopamine to Smoothened," Genes & Development, 16:2743-2748 (2002).
Creighton, C. J., "A gene transcription signature of the Akt/mTOR pathway in clinical breast tumors," Oncogene, 26:4648-4655 (2007).
Dellovade, T., et. al., "The Hedgehog Pathway and Neurological Disorders," Annu. Rev. Neurosci, 29:539-563 (2006).
Dorsam, R. T. and Gutkind, J.S., et. al., "G-protein-coupled receptors and cancer," Nature Reviews Cancer, 7(2):79-94 (2007).
Engelman, J.A. and Settlemen, J., "Acquired Resistance to Tyrosine Kinase Inhibitors During Cancer Therapy," 18(1):73-79 (2008).
Goodrich, L. V., et. al., "Altered Neural Cell Fates and Medulloblastoma in Mouse *patched* Mutants," Science, 277:1109-1113 (1997).
Goudet, C., et. al., "Allosteric modulators of class-C G-protein-coupled receptors open new possibilities for therapeutic application," Drug Discovery Today, 1(1):125-133 (2004).
Grachtchouk, M., et. al., "Basal cell carcinomas in mice overexpressing *Gli2* in skin," Nature Genetics, 24:216-217 (2000).
Han, Y., et al., "Dual and Opposing Roles of Primary Cilia in Medulloblastoma Development," 15(9):1062-1065 (2009).
Hartmann, W., et. al., "Phosphatidylinositol 3'-Kinase/AKT Signaling Is Activated in Medulloblastoma Cell Proliferation and Is Associated with Reduced Expression of *PTEN*," Clin Cancer Res, 12(10):3019-3027 (2006).
Hyman, J., et al., "Small-Molecule Inhibitors Reveal Multiple Strategies for Hedgehog Pathway Blockade," PNAS, 106(33):14132-14137 (2009).
Kim, J. and Diehl, J.A., "Nuclear Cyclin D1: An Oncogenic Driver in Human Cancer," J Cell Physiol., 220(2):292-296 (2009).
Kool, M., et al., "Integrated Genomics Identifies Five Medulloblastoma Subtypes with Distinct Genetic Profiles, Pathway Signatures and Clinicopathological Features," PLoS One, 3(8) e3088 (1-14) (2008).
Krause, D., et al., "Tyrosine Kinases as Targets for Cancer Therapy," New England Journal of Medicine, 353:172-187 (2005).

(Continued)

*Primary Examiner* — Misook Yu
*Assistant Examiner* — Julie Wu
(74) *Attorney, Agent, or Firm* — Ropes & Gray LLP

(57) ABSTRACT

The emergence of mutations in tyrosine kinases following treatment of cancer patients with molecular-targeted therapy represents a major mechanism of acquired drug resistance. Here, we describe a mutation in the serpentine receptor, Smoothened (SMO), which results in resistance to a Hedgehog (Hh) pathway inhibitor in medulloblastoma. A single amino acid substitution in a conserved aspartic acid residue of SMO maintains Hh signaling, but results in the inability of the Hh pathway inhibitor, GDC-0449, to bind SMO and suppress the pathway. This mutation was not only acquired in a GDC-0449-resistant mouse model of medulloblastoma, but was identified in a Medulloblastoma patient following relapse on GDC-0449. The invention provides screening methods to detect SMO mutations and methods to screen for drugs that specifically modulate mutant SMO exhibiting drug resistance.

16 Claims, 21 Drawing Sheets

(56) References Cited

OTHER PUBLICATIONS

Maira, S., et al., "P13K Inhibitors for Cancer Treatment: Where do We Stand?" Biochem. Soc. Trans. 37:265-272 (2009).
Molckovsky, A. and Siu, L.L., "First-in-class, first-in-human phase I results of targeted agents: Highlights of the 2008 American Society of Clinical Oncology meeting," Journal of Hematology & Oncology, 1:20 (9 pages)(2008).
Murone, M., et. al., "Sonic hedgehog signaling by the Patched-Smoothened receptor complex," Current Biology, 9:76-84 (1999).
Northcott, P. A., et. al., "Multiple recurrent genetic events converge on control of histone lysine methylation in medulloblastoma," Nature Genetics, 41(4):465-472 (2009).
Oliver, T., et al., "Transcriptional Profiling of the Sonic Hedgehog Response: A Critical Role for N-myc in Proliferation of Neuronal Precursors," PNAS, 100(12):7331-7336 (2003).
Pogoriler, J., et al., "Loss of Cyclin D1 Impairs Cerebellar Development and Suppresses Medulloblastoma Formation," Development, 133(19):3929-3937 (2006).
Polkinghorn, W. and Tarbell, N.J., "Medulloblastoma: Tumorigenesis, Current Clinical Paradigm, and Efforts to Improve Risk Stratification," Nat. Clin. Pract. Oncol., 4(5):295-304 (2007).
Remsberg, J.R., et al., "Structural Analogues of Smoothened Intracellular Loops as Potent Inhibitors of Hedgehog Pathway and Cancer Cell Growth," Journal of Medicinal Chemistry, 50(18):4534-4538 (2007).
Robarge, K.D., et al., "GDC-0449-a Potent Inhibitor of the Hedgehog Pathway," Bioorganic & Medicinal Chemistry Letters,19(19):5576-5581 (2009).
Roessler, E., et. al., "A previously unidentified amino-terminal domain regulates transcriptional activity of wild-type and disease-associated human GLI2," Human Molecular Genetics, 14(15):2181-2188 (2005).
Rohatgi, R., et al., Hedgehog Signal Transduction by Smoothened: Pharmacologic Evidence for 2-Step Activation Process, PNAS, 106(9):3196-3201 (2009).
Romer, J., et al., "Suppression of the Shh Pathway Using a Small Molecule Inhibitor Eliminates Medulloblastoma in Ptc1$^{+/-}$p53$^{-/-}$ Mice," Cancer Cell, 6:229-240 (2004).
Rosenbaum, D. M., et. al., "The structure and function of G-protein-coupled receptors," Nature, 459:356-363 (2009).
Rubin, L. L. and deSauvage, F.J., "Targeting the Hedgehog pathway in cancer," Nature Reviews Drug Discovery, 5:1026-1033 (2006).
Rudin, C. M., et al., "Treatment of Medulloblastoma with Hedgehog Pathway Inhibitor GDC-0449," New England Journal of Medicine, 361(12):1173-1178 (XP007915450) (2009).
Saal, L., et al., "Poor Prognosis in Carcinoma is Associated with a Gene Expression Signature of Aberrant PTEN Tumor Suppressor Pathway Activity," PNAS, 104(18):7564-7569 (2007).
Taipale, J., et al., "Effects of Oncogenic Mutations in Smoothened and Patched can be Reversed by Cyclopamine," Nature, 406(6799):1005-1009 (2000).
Taylor, M. D., et. al., "Mutations in SUFU predispose to medulloblastoma," Nature Genetics, 31:306-310 (2002).
Vivanco, I. and Sawyers, C.L., et. al., "The Phosphatidylinositol 3-Kinase AKT Pathway in Human Cancer," Nature Reviews Cancer, 2:489-501 (2002).
Wang, Y., et al., "Selective Translocation of Intracellular Smoothened to the Primary Cilium in Response to Hedgehog Pathway Modulation," PNAS, 106(8):2623-2628 (2009).
Wetmore, C., et al., Loss of *p53* but not *ARF* Accelerates Medulloblastoma in Mice Heterozygous for *patched*, Cancer Research, 61:513-516 (2001).
Wilson, C., et al., "Smoothened Adopts Multiple Active and Inactive Conformations Capable of Trafficking to the Primary Cilium," PLoS One, 4(4), e5182 (2009).
Wong, H., et al., "Preclinical Assessment of the Absorption, Distribution, Metabolism and Excretion of GDC-0449 (2-chloro-N-(4-chloro-3-(pyridin-2-yl)phenyl-4-(methylsulfonyl) benzamide, an Orally Bioavailable Systemic Hedgehog Signalling Pathway Inhibitor," Xenobiotica, 39(11):850-861 (2009).
Xie, J., et al., "Activating Smoothened Mutations in Sporadic Basal-Cell Carcinoma," Nature, 391:90-92 (1998).
Yauch, R. L., et. al., "A paracrine requirement for hedgehog signalling in cancer," Nature, 455(7211):406-410 (XP002520120) (2008).
Yauch, R. L., et. al., "*Smoothened* Mutation Confers Resistance to a Hedgehog Pathway Inhibitor in Medulloblastoma," Science, 326(5952):572-574 (XP007915400) (2009).
Zindy, F., et. al., "Genetic alterations in Mouse Medulloblastomas and Generation of Tumors *De novo* from Primary Cerebellar Granule Neuron Precursors," Cancer Res, 67(6):2676-2684 (2007).
Zurawel, R. H., et. al., "Analysis of PTCH/SMO/SHH Pathway Genes in Medulloblastoma," Genes, Chromosomes & Cancer, 27(1):44-51 (2000).
SMO-Human, Jul. 28, 2009, Full=Smoothened homolog; Short=SMO; AltName: Full=GX protein; Flags: Precursor, Access No. 099835, date of search: Jul. 29, 2014.

* cited by examiner

FIG. 6

| DNA source | 7q31.2 (SMO) copy number | | |
|---|---|---|---|
| | predicted (Affy 100K) | assay 1 | assay2 |
| biopsy after relapse | | 2.2 | 2.4 |
| control cell line-1 | 2.1 | 1.9 | 2.2 |
| control cell line-2 | 3.4 | 4.5 | 3.9 |
| control cell line-3 | 1.1 | 1.2 | 1.2 |

SEQUENCE LISTING

<160> NUMBER OF SEQ ID NOS: 15

<210> SEQ ID NO 1
<211> LENGTH: 787
<212> TYPE: PRT
<213> ORGANISM: Homo sapiens -continued

```
<400> SEQUENCE: 1

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
            20                  25                  30

Ser Gly Asn Ala Thr Gly Pro Gly Pro Arg Ser Ala Gly Gly Ser Ala
        35                  40                  45

Arg Arg Ser Ala Ala Val Thr Gly Pro Pro Pro Leu Ser His Cys
50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285

Ala Arg Arg Glu Ile Val Cys Arg Ala Asp Gly Thr Met Arg Leu Gly
290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
            340                 345                 350

Leu Ser Gly Lys Thr Ser Tyr Phe His Leu Leu Thr Trp Ser Leu Pro
        355                 360                 365

Phe Val Leu Thr Val Ala Ile Leu Ala Val Ala Gln Val Asp Gly Asp
370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415
```

```
Tyr Phe Leu Ile Arg Gly Val Met Thr Leu Phe Ser Ile Lys Ser Asn
            420                 425                 430

His Pro Gly Leu Leu Ser Glu Lys Ala Ala Ser Lys Ile Asn Glu Thr
        435                 440                 445

Met Leu Arg Leu Gly Ile Phe Gly Phe Leu Ala Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510

Pro Ser Leu Leu Val Glu Lys Ile Asn Leu Phe Ala Met Phe Gly Thr
        515                 520                 525

Gly Ile Ala Met Ser Thr Trp Val Trp Thr Lys Ala Thr Leu Leu Ile
530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
610                 615                 620

Met Val Ala Arg Arg Gly Ala Ile Leu Pro Gln Asp Ile Ser Val Thr
625                 630                 635                 640

Pro Val Ala Thr Pro Val Pro Glu Glu Gln Ala Asn Leu Trp Leu
                645                 650                 655

Val Glu Ala Glu Ile Ser Pro Glu Leu Gln Lys Arg Leu Gly Arg Lys
            660                 665                 670

Lys Lys Arg Arg Lys Arg Lys Lys Glu Val Cys Pro Leu Ala Pro Pro
        675                 680                 685

Pro Glu Leu His Pro Ala Pro Ala Pro Ser Thr Ile Pro Arg Leu
690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Pro Gln Asp Pro Phe Leu Pro Ser Ala
            740                 745                 750

Pro Ala Pro Val Ala Trp Ala His Gly Arg Arg Gln Gly Leu Gly Pro
        755                 760                 765

Ile His Ser Arg Thr Asn Leu Met Asp Thr Glu Leu Met Asp Ala Asp
770                 775                 780

Ser Asp Phe
785

<210> SEQ ID NO 2
<211> LENGTH: 787
<212> TYPE: PRT
<213> ORGANISM: Homo sapiens
```

```
<220> FEATURE:
<221> NAME/KEY: MISC_FEATURE
<222> LOCATION: (473)..(473)
<223> OTHER INFORMATION: Xaa is any amino acidother than D

<400> SEQUENCE: 2

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285

Ala Arg Arg Glu Ile Val Cys Arg Ala Asp Gly Thr Met Arg Leu Gly
290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Leu Thr
                325                 330                 335

Tyr Ala Trp His Thr Ser Phe Lys Ala Leu Gly Thr Thr Tyr Gln Pro
            340                 345                 350

Leu Ser Gly Lys Thr Ser Tyr Phe His Leu Leu Thr Trp Ser Leu Pro
        355                 360                 365

Phe Val Leu Thr Val Ala Ile Leu Ala Val Ala Gln Val Asp Gly Asp
370                 375                 380
```

```
Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
            420                 425                 430

His Pro Gly Leu Leu Ser Glu Lys Ala Ala Ser Lys Ile Asn Glu Thr
        435                 440                 445

Met Leu Arg Leu Gly Ile Phe Gly Phe Leu Ala Phe Gly Phe Val Leu
    450                 455                 460

Ile Thr Phe Ser Cys His Phe Tyr Xaa Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510

Pro Ser Leu Leu Val Glu Lys Ile Asn Leu Phe Ala Met Phe Gly Thr
        515                 520                 525

Gly Ile Ala Met Ser Thr Trp Val Trp Thr Lys Ala Thr Leu Leu Ile
    530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
610                 615                 620

Met Val Ala Arg Arg Gly Ala Ile Leu Pro Gln Asp Ile Ser Val Thr
625                 630                 635                 640

Pro Val Ala Thr Pro Val Pro Glu Glu Gln Ala Asn Leu Trp Leu
                645                 650                 655

Val Glu Ala Glu Ile Ser Pro Glu Leu Gln Lys Arg Leu Gly Arg Lys
            660                 665                 670

Lys Lys Arg Arg Lys Arg Lys Lys Glu Val Cys Pro Leu Ala Pro Pro
        675                 680                 685

Pro Glu Leu His Pro Ala Pro Ala Pro Ser Thr Ile Pro Arg Leu
    690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Gln Asp Pro Phe Leu Pro Ser Ala
            740                 745                 750

Pro Ala Pro Val Ala Trp Ala His Gly Arg Arg Gln Gly Leu Gly Pro
        755                 760                 765

Ile His Ser Arg Thr Asn Leu Met Asp Thr Glu Leu Met Asp Ala Asp
    770                 775                 780

Ser Asp Phe
785
```

<210> SEQ ID NO 3
<211> LENGTH: 2364
<212> TYPE: DNA
<213> ORGANISM: Homo sapiens

<400> SEQUENCE: 3

| | | | | | | |
|---|---|---|---|---|---|---|
| atggccgctg | cccgcccagc | gcggggggccg | gagctcccgc | tcctggggct | gctgctgctg | 60 |
| ctgctgctgg | gggacccggg | ccggggggcg | gcctcgagcg | ggaacgcgac | cgggcctggg | 120 |
| cctcggagcg | cgggcgggag | cgcgaggagg | agcgcggcgg | tgactggccc | tccgccgccg | 180 |
| ctgagccact | gcggccgggc | tgccccctgc | gagccgctgc | gctacaacgt | gtgcctgggc | 240 |
| tcggtgctgc | cctacggggc | cacctccaca | ctgctggccg | gagactcgga | ctcccaggag | 300 |
| gaagcgcacg | gcaagctcgt | gctctggtcg | ggcctccgga | tgcccccccg | ctgctgggca | 360 |
| gtgatccagc | ccctgctgtg | tgccgtatac | atgcccaagt | gtgagaatga | ccgggtggag | 420 |
| ctgcccagcc | gtaccctctg | ccaggccacc | cgaggcccct | gtgccatcgt | ggagagggag | 480 |
| cggggctggc | ctgacttcct | gcgctgcact | cctgaccgct | tccctgaagg | ctgcacgaat | 540 |
| gaggtgcaga | acatcaagtt | caacagttca | ggccagtgcg | aagtgccctt | ggttcggaca | 600 |
| gacaaccccca | agagctggta | cgaggacgtg | gagggctgcg | gcatccagtg | ccagaacccg | 660 |
| ctcttcacag | aggctgagca | ccaggacatg | cacagctaca | tcgcggcctt | cggggccgtc | 720 |
| acgggcctct | gcacgctctt | caccctggcc | acattcgtgg | ctgactgcg | gaactcgaat | 780 |
| cgctaccctg | ctgttattct | cttctacgtc | aatgcgtgct | tctttgtggg | cagcattggc | 840 |
| tggctggccc | agttcatgga | tggtgcccgc | cgagagatcg | tctgccgtgc | agatggcacc | 900 |
| atgaggcttg | gggagcccac | ctccaatgag | actctgtcct | gcgtcatcat | ctttgtcatc | 960 |
| gtgtactacg | ccctgatggc | tggtgtggtt | tggtttgtgg | tcctcaccta | tgcctggcac | 1020 |
| acttccttca | aagccctggg | caccacctac | cagcctctct | cgggcaagac | ctcctacttc | 1080 |
| cacctgctca | cctggtcact | ccccttgtc | ctcactgtgg | caatccttgc | tgtggcgcag | 1140 |
| gtggatgggg | actctgtgag | tggcatttgt | tttgtgggct | acaagaacta | ccgataccgt | 1200 |
| gcgggcttcg | tgctggcccc | aatcggcctg | gtgctcatcg | tgggaggcta | cttcctcatc | 1260 |
| cgaggagtca | tgactctgtt | ctccatcaag | agcaaccacc | ccgggctgct | gagtgagaag | 1320 |
| gctgccagca | agatcaacga | gaccatgctg | cgcctgggca | tttttggctt | cctggccttt | 1380 |
| ggctttgtgc | tcattacctt | cagctgccac | ttctacgact | tcttcaacca | ggctgagtgg | 1440 |
| gagcgcagct | ccgggactta | tgtgctatgt | caggccaatg | tgaccatcgg | gctgcccacc | 1500 |
| aagcagccca | tccctgactg | tgagatcaag | aatcgcccga | gccttctggt | ggagaagatc | 1560 |
| aacctgtttg | ccatgtttgg | aactggcatc | gccatgagca | cctgggtctg | gaccaaggcc | 1620 |
| acgctgctca | tctggaggcg | tacctggtgc | aggttgactg | ggcagagtga | cgatgagcca | 1680 |
| aagcggatca | agaagagcaa | gatgattgcc | aaggccttct | ctaagcggca | cgagctcctg | 1740 |
| cagaacccag | gccaggagct | gtccttcagc | atgcacactg | tgtcccacga | cgggcccgtg | 1800 |
| gcgggcttgg | cctttgacct | caatgagccc | tcagctgatg | tctcctctgc | ctgggcccag | 1860 |
| catgtcacca | agatggtggc | tcggagagga | gccatactgc | cccaggatat | ttctgtcacc | 1920 |
| cctgtggcaa | ctccagtgcc | cccagaggaa | caagccaacc | tgtggctggt | tgaggcagag | 1980 |
| atctccccag | agctgcagaa | gcgcctgggc | cggaagaaga | agaggaggaa | gaggaagaag | 2040 |
| gaggtgtgcc | cgctggcgcc | gccccctgag | cttcaccccc | ctgccctgc | ccccagtacc | 2100 |
| attcctcgac | tgcctcagct | gccccggcag | aaatgcctgg | tggctgcagg | tgcctgggga | 2160 |

```
gctggggact cttgccgaca gggagcgtgg accctggtct ccaacccatt ctgcccagag    2220
cccagtcccc ctcaggatcc atttctgccc agtgcaccgg cccccgtggc atgggctcat    2280
ggccgccgac agggcctggg gcctattcac tcccgcacca acctgatgga cacagaactc    2340
atggatgcag actcggactt ctga                                          2364
```

```
<210> SEQ ID NO 4
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 4
gcaggacatt ccacacagtt cttg                                            24

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 5
ataggtgctg ggatacaggc ttg                                             23

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 6
taccctgaca ccaatctcct caacg                                           25

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 7
ggaattccca tcttcccaac tcc                                             23

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 8
agatggctga gtgggtaaag g                                               21

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 9
gtggaggtca gaggacaaac tt                                              22
```

```
<210> SEQ ID NO 10
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 10
agaaggtgac ctggatgaga                                       20

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 11
tgatacatat ggcggtcaat ct                                    22

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide Probe

<400> SEQUENCE: 12
cttctcagga gataccggga atccaag                               27

<210> SEQ ID NO 13
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 13
tcagctgcca cttctac                                          17

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 14
tcagctgcca cttctacg                                         18

<210> SEQ ID NO 15
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 15
tcagctgcca cttctacc                                         18
```

MUTANT SMOOTHENED AND METHODS OF USING THE SAME

CROSS-REFERENCE TO RELATED APPLICATIONS

This application is a national stage filing under 35 U.S.C. 371 of International Application No. PCT/US2010/047739, filed on Sep. 2, 2010, which claims the benefit of U.S. Provisional Application No. 61/239,364, filed Sep. 2, 2009. The specifications of each of the foregoing applications are hereby incorporated by reference in their entirety. International Application No. PCT/US2010/047739 was published under PCT Article 21(2) in English.

FIELD OF THE INVENTION

The present invention relates to isolated mutant SMO nucleic acids and proteins related to chemotherapeutic resistance of tumors and methods of screening for compounds that bind to SMO mutants, or modulate SMO activity, and to cancer diagnostics and therapies and in particular to the detection of mutations that are diagnostic and/or prognostic and treatment of drug-resistant tumors.

BACKGROUND OF THE INVENTION

Molecular-targeted cancer therapeutics have shown impressive activity in the clinic. Some of the best noted examples include the tyrosine kinase inhibitors imatinib in Philadelphia chromosome-positive chronic myelogenous leukemia (CML) or KIT/PDGFR-mutant gastrointestinal stromal tumors (GISTs) and erlotinib in EGFR-mutant non-small cell lung cancer (NSCLC) (Krause, D. S. and R. A. Van Etten (2005) *N. Engl. J. Med.* 353(2):172-187). Treatment with these agents has led to dramatic anti-tumor responses in patient populations harboring these molecular abnormalities. However, despite the impressive initial clinical responses, most patients eventually progress due to the acquisition of drug resistance (Engelman, J. A. and J. Settleman (2008) *Curr. Opin. Genet. Dev.* 18(1):73-79). Identification of mechanisms of resistance have consequently opened the door to more rational drug combinations and the development of "second-generation" inhibitors that can potentially overcome or avoid the emergence of resistance.

Medulloblastoma is a primitive neuroectodermal tumor of the cerebellum that represents the most common brain malignancy in children (Polkinghorn, W. R. and N. J. Tarbell (2007) *Nat. Clin. Pract. Oncol.* 4(5):295-304). Despite improvements in survival rates, the debilitating side effects of adjuvant radiation represent a major clinical challenge, thus supporting the need for new molecular targeted therapies.

The Hedgehog (Hh) signaling pathway has been directly implicated in the pathogenesis of medulloblastoma. Constitutive Hh signaling, most often due to underlying loss of function mutations in the inhibitory receptor PTCH1, has been demonstrated in approximately 30% of sporadic cases (Zurawel, R. H. et al. (2000) *Genes Chromosomes Cancer* 27(1):44-51; Kool, M. et al. (2008) *PLoS ONE* 3(8):e3088; Dellovade, T. et al. (2006) *Annu. Rev. Neurosci.* 29:539; Rubin, L. L. and F. J. de Sauvage (2006) *Nat. Rev. Drug Discov.* 5:1026). Mice heterozygous for Ptch1 (Ptch1$^{+/-}$) can spontaneously develop medulloblastoma and treatment with Hh pathway inhibitors results in tumor elimination and prolonged survival (Goodrich, L. V. et al. (1997) *Science* 277 (5329):1109-1113; Romer, J. T. et al. (2004) *Cancer Cell* 6(3):229-240). However, it has recently been observed that a patient treated with the novel Hh pathway inhibitor, GDC-0449 initially showed a dramatic response to treatment (Charles M. Rudin et al. (2009) *N. Engl. J. Med.* (submitted)), only to fail to have a durable response to treatment and a relapse of the tumor.

There is an urgent need in the art to find compounds that modulate SMO activity in such mutant SMO proteins to overcome drug resistance upon treatment with GDC-0449. There is further a need to a method to diagnose patients who may be resistant to treatment either through natural variation of their SMO genotype or through acquired mutation and resistance.

SUMMARY OF THE INVENTION

The invention provides isolated nucleic acid molecules encoding a mutant SMO protein. In one aspect, the nucleic acid molecules encode an amino acid sequence that is at least 95% identical to SEQ ID NO:2 wherein said amino acid sequence comprises an amino acid at position 473 of SEQ ID NO:2 that is any amino acid other than aspartic acid (D). In some embodiments, the amino acid at position 473 of SEQ ID NO:2 is histidine (H), glycine (G), phenylalanine (F), tyrosine (Y), leucine (L), isoleucine (I), proline (P), serine (S), threonine (T), methionine (M), glutamine (Q), or asparagine (N). In one aspect of the invention, the isolated nucleic acid sequence comprising a parental nucleic acid sequence of SEQ ID NO:3 (wild-type SMO), but containing a mutation or mutations at positions 1417, 1418 and/or 1419 that changes the encoded amino acid from aspartic acid (D) to a different amino acid. In some embodiments, the mutations result in a change from aspartic acid (D) to histidine (H), glycine (G), phenylalanine (F), tyrosine (Y), leucine (L), isoleucine (I), proline (P), serine (S), threonine (T), methionine (M), glutamine (Q), or asparagine (N).

In another aspect, the invention provides nucleic acid probes capable of specifically hybridizing to a nucleic acid encoding a mutated SMO protein or fragment thereof incorporating a mutation in amino acid 473 of SMO. In one embodiment, he probe is complementary to the nucleic acid encoding the mutated SMO or said fragment thereof. The probe may have a length of about 10 to about 50 nucleotides. In some embodiments, the probe may be detectably labeled. The probe differentially binds mutant Smo over wild-type Smo (having an aspartic acid at position 473).

The invention also provides an isolated mutant SMO protein comprising an amino acid sequence of that is at least 95% identical to SEQ ID NO:2 wherein the amino acid sequence comprises an amino acid at position 473 other than aspartic acid (D). In some embodiments, the amino acid at position 473 is histidine (H), glycine (G), phenylalanine (F), tyrosine (Y), leucine (L), isoleucine (I), proline (P), serine (S), threonine (T), methionine (M), glutamine (Q), or asparagine (N).

The invention further provides an antibody that specifically binds to the mutant SMO protein of the invention wherein the epitope of the antibody is present on a mutant SMO having an amino acid other than aspartic acid at position 473, but does not bind to wild-type SMO. In some embodiments, the antibody binds with high affinity to mutant SMO, but does not bind with high affinity to wild-type SMO. In some embodiments, the antibody is a monoclonal antibody, a chimeric antibody, a humanized antibody, a single chain antibody or an antigen-binding fragment thereof (e.g., a Fab, a Fab', a F(ab')$_2$, or an Fv fragment). In some embodiments, the antibody is conjugated to a detectable label. In other embodiments, the antibody is conjugated to a cytotoxic agent, such as, but not limited to a chemotherapeutic agent, a toxin or a radioactive isotope. In some embodiments, the antibody inhibits SMO activity. In other embodiments, the antibody inhibits only mutant SMO activity.

The invention also provides a method of detecting a mutated SMO gene in a sample comprising amplifying from a sample a nucleic acid encoding the carboxy-terminus of transmembrane domain 6 of SMO, or a fragment thereof suspected of containing a mutation, and comparing the electrophoretic mobility of the amplified nucleic acid to the electrophoretic mobility of corresponding wild-type SMO gene or fragment thereof. In some embodiments, the electrophoretic mobility is determined on polyacrylamide gel. In such embodiments, the electrophoretic mobility of mutant Smo can be differentiated from wild-type Smo.

The invention further provides a method of identifying at least one SMO mutation in a sample comprising contacting a nucleic acid from the sample with a nucleic acid probe that is capable of specifically hybridizing to a nucleic acid encoding a mutated SMO protein, or fragment thereof incorporating a mutation, and detecting hybridization. In some embodiments, the method detects a mutation in the carboxy-terminal portion of transmembrane domain 6 of SMO. In some embodiments, the SMO mutation occurs in Smo at positions 1417, 1418, and/or 1419 (encoding amino acid at position 473) wherein the mutation results in a codon encoding an amino acid other than aspartic acid. In some embodiments the probe is detectably labeled. In some embodiments the probe is an antisense oligomer. In some embodiments the nucleic acid of the SMO gene or a fragment thereof in the sample is amplified and contacted with the probe.

The invention also provides a method for identifying a tumor in a human subject that is resistant to treatment with a chemotherapeutic agent such as GDC-0449 comprising determining the presence of a mutated SMO gene or mutated SMO protein in a sample of the tumor wherein said mutation is located in the SMO gene that encodes a portion of SMO at the extracellular membrane surface (e.g., the carboxy-terminal portion of transmembrane domain 6 of SMO) whereby the presence of the mutated SMO gene or mutated SMO protein indicates that the tumor is resistant to treatment with the chemotherapeutic agent, such as, but not limited to GDC-0449. In some embodiments the chemotherapeutic agent is GDC-0449. In other embodiments, the chemotherapeutic agent is cyclopamine. In some embodiments, the mutation is in a portion of the SMO gene that encodes amino acid 473 of SMO. In some embodiments, the mutation causes a change in amino acid 473 of SMO from Asp to another amino acid. In some embodiments the other amino acid is histidine (H), glycine (G), phenylalanine (F), tyrosine (Y), leucine (L), isoleucine (I), proline (P), serine (S), threonine (T), methionine (M), glutamine (Q), or asparagine (N).

The invention also provides a method for identifying a tumor in a human subject that is susceptible to treatment with an SMO inhibitor comprising (i) determining the presence of a wild-type SMO protein or gene in a sample of the tumor whereby the presence of a wild-type SMO protein or gene indicates that the tumor is susceptible to treatment with a SMO inhibitor or (ii) determining the presence of a mutated SMO protein or gene in a sample of the tumor wherein the mutation results in a change of amino acid at position 473 of SMO, whereby the presence of a mutated SMO protein or gene indicates that the tumor is not susceptible to treatment with a SMO inhibitor such as GDC-0449. In some embodiments, the SMO mutation is a change from aspartic acid (D) 473 to any other amino acid. In some embodiments, the amino acid is histidine (H), glycine (G), phenylalanine (F), tyrosine (Y), leucine (L), isoleucine (I), proline (P), serine (S), threonine (T), methionine (M), glutamine (Q), or asparagine (N).

The invention also provides a method of determining prognosis of patient being treated for a Hedgehog-dependent tumor comprising determining in a sample of a tumor the presence or absence of a mutation at amino acid 473 whereby the presence of the mutation indicates poorer prognosis compared to the absence of said mutation using certain Smo inhibitors.

The invention further provides a method of screening for compounds that inhibit signaling of a mutant SMO protein that incorporates a mutation at amino acid 473 comprising contacting the mutant SMO with a test compound and detecting binding of the compound to the mutant SMO whereby binding of the test compound to mutant SMO indicates that the test compound is an inhibitor of mutant SMO.

The invention also provides a method of screening for compounds that inhibit signaling of a mutant SMO protein that incorporates a mutation at amino acid 473 comprising contacting a cell that expresses the mutant SMO with a test compound and detecting activity of Gli in the cell whereby the presence of Gli activity indicates that the test compound is not an inhibitor of mutant SMO. In some embodiments, Gli activity is measured using a Gli protein that is conjugated to a detectable label. In some embodiments, the detectable label is a fluorescent label (e.g., luciferase).

The invention also provides a method for treating cancer by administering to a patient in need thereof a compound that specifically binds to SMO having an amino acid substitution (mutation) at position 473. In some embodiments, the mutant SMO protein comprises the substitution from aspartic acid at 473 to any other amino acid. In some embodiments, the other amino acid is histidine (H), glycine (G), phenylalanine (F), tyrosine (Y), leucine (L), isoleucine (I), proline (P), serine (S), threonine (T), methionine (M), glutamine (Q), or asparagine (N). In some embodiments the compound is an antibody. In some embodiments, the compound is a small molecule having the structural formula of Formula I, Formula II and/or Formula III (see below).

The invention also provides a method for delaying or preventing drug-induced mutagenesis comprising administering an inhibitor of SMO and a PI3K inhibitor. In some embodiments the SMO inhibitor is GDC-0449. In some embodiments the SMO inhibitor is an inhibitor of a mutant SMO having an amino acid substitution at position 473. In some embodiments the mutant SMO inhibitor is a compound having the structural formula of Formula I, Formula II or Formula III (see below).

BRIEF DESCRIPTION OF THE DRAWINGS

FIG. 6 shows no SMO copy number alterations were detected by qPCR using 2 independent assays from gDNA derived from the biopsy at progression. Copy number was determined by qPCR and calibrated to normal human genomic DNA following normalization to LINE-1. As controls, gDNA from cell lines with low-level copy number changes at the SMO locus, as determined previously by Affymetrix 100K array profiling (predicted), were utilized.

The vehicle control curve stops at day 8, since mice were euthanized when their tumor burden reached 2000 mm³. (B) assessment of mGli1 mRNA levels by qRT-PCR in tumors from panel (A) collected 6 hours after the last drug treatment. Values represent means±SDs. (C) representative images of S12 cells treated with indicated compounds in the absence (top) or presence (bottom) of Shh for 16 hours. Cilia and centrosomes (acetylated and gamma tubulins respectively, as well as Smo were detected by immunofluorescence, while nuclei were visualized by DAPI staining. A single overlay of all three channels is shown with the (Smo) channel shifted six pixels to the right. Arrows point to cilia with robust (grey) and weak or no (white) Smo staining Scale bar is 15 µM. (D) bar graph depicting the % S12 cells with Smo+cilia (grey arrows) under the indicated conditions, calculated from multiple images similar to those shown in panel (C). At least 200 cilia from three or more experiments were evaluated and values represent mean±SD. To facilitate comparison, the level of ciliary Smo in vehicle (DMSO) treated cells is indicated with a dotted ( - - - ) line for the –Hh condition (grey bars) and a dashed ( - - - ) line for the +Hh condition (black bars).

Figure 16:
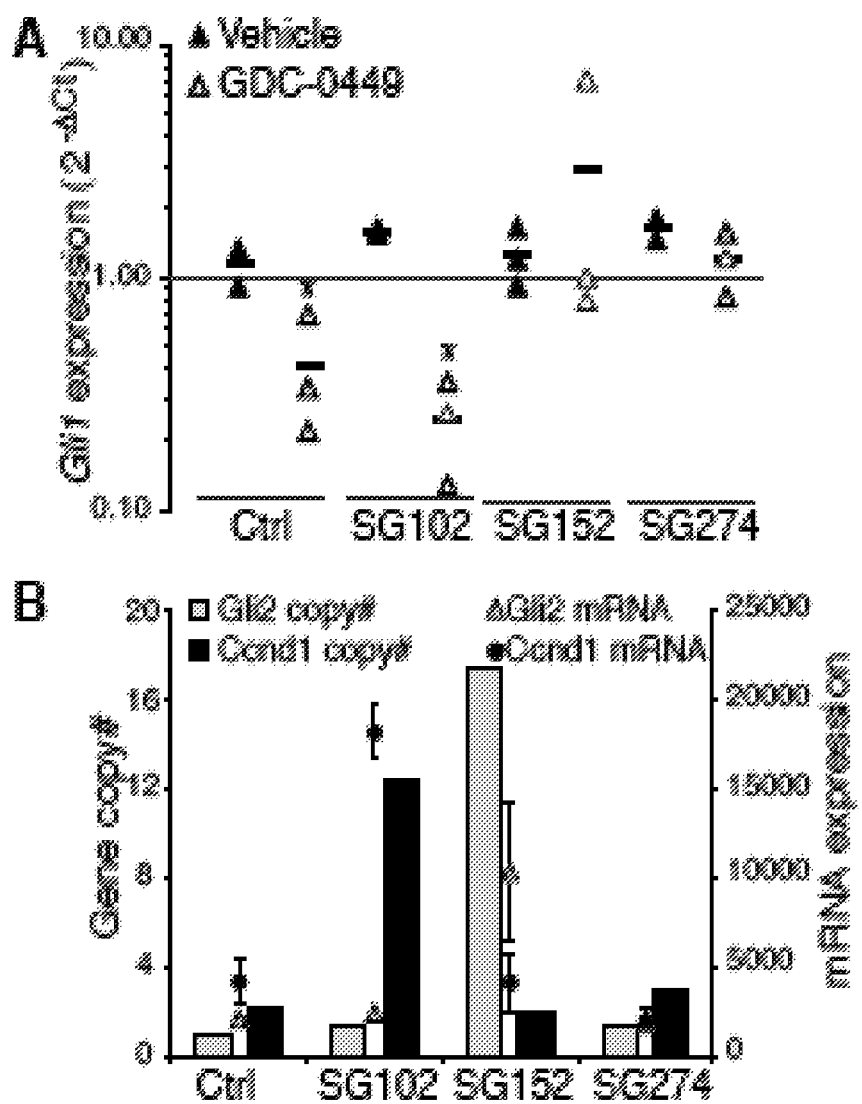
Figure 16:
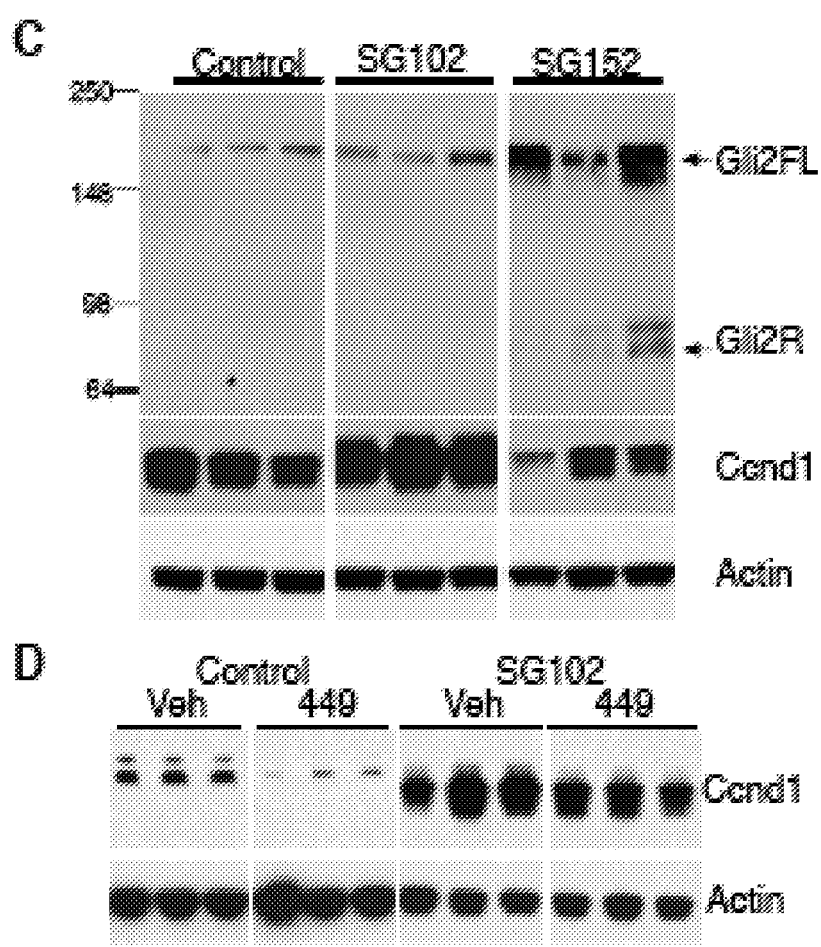

FIG. 16 shows the molecular characterization of additional resistant MB allograft models reveals mechanisms of GDC-0449 resistance downstream of Smo. (A) quantification of Gli1 mRNA levels by qRT-PCR in expanded tumors (n=3) collected 6 hours after treatment with either vehicle (closed triangles) or GDC-0449 (open triangles). Gli1 was similarly expressed in all models, but only significantly down regulated by GDC-0449 in control and SG102 tumors ($*p<0.02$). (B) graph simultaneously showing the copy number (bars) and mRNA expression (data points) of Ccnd1 (black) and Gli2 (grey) in control and GDC-0449-resistant tumors. Gene copy number analysis was performed by qPCR of the initial resistant tumor to confirm gene amplifications observed by aCGH, while mRNA expression was determined by micro-array profiling of three expanded tumors. mRNA expression levels are shown in arbitrary units and represent means±SDs. (C) immunoblots showing Ccnd1 and Gli2 protein levels. Three expanded tumors were analyzed for each tumor line and actin levels are shown as a loading control. Gli2FL and Gli2R represent the full length and repressor forms of Gli2. The positions of molecular weight markers are indicated on the left of the Gli2 immunoblot in kilo Daltons (kDa). (D) immunoblot showing Ccnd1 protein levels in expanded control and SG102 tumors (n=3/group) following a 24-hour treatment with either vehicle (Veh) or GDC-0449 (449). The Hh-target gene Ccnd1 is refractory to GDC-0449 mediated down regulation in SG102 tumors.

Figure 17:
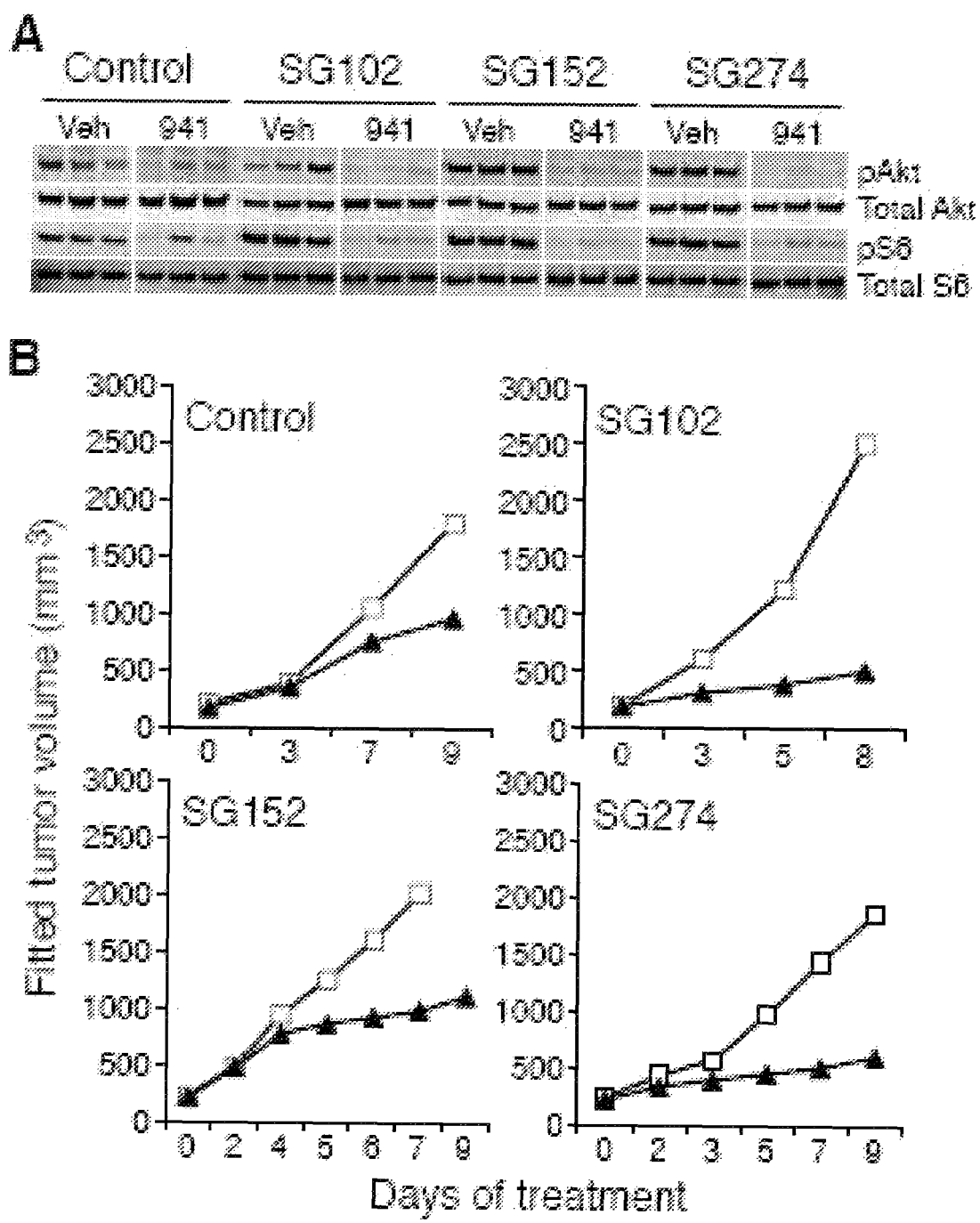

FIG. 17 shows that control and GDC-0449-resistant MB allografts are sensitive to PI3K inhibition. A, immunoblots showing levels of activated AKT and S6 in expanded tumors of the four models (n=3/group) following a 6-hour treatment with either vehicle (Veh) or GDC-0941 (941). Total AKT and S6 levels are shown as loading controls. B, mean fitted tumor volumes of control and GDC-0449-resistant MB allografts treated orally with either vehicle (open squares) or 150 mg kg-1 GDC-0941 once daily (solid triangles). An equal number of animals were analyzed for both treatment arms of each tumor model: Control (n=7), SG102 (n=5), SG152 (n=5) and SG274 (n=7).

Figure 18:
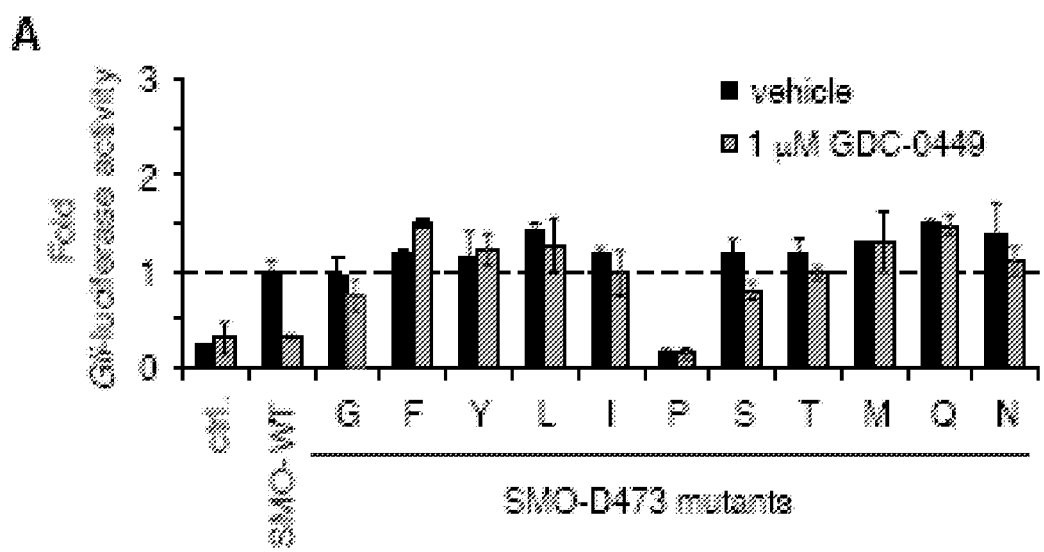
Figure 18:
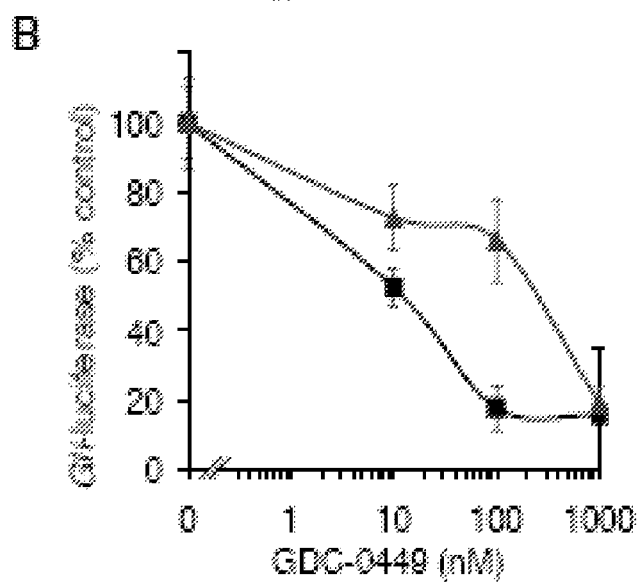
Figure 18:
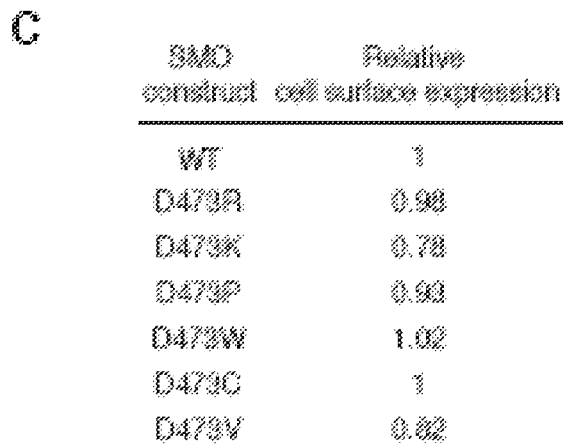

FIG. 18 shows GDC-0449 inhibition and cell surface expression of various SMO-D473 mutants. (A) as in FIG. 1A, but with various other amino acid substitutions at position 473. (B) Gli-luciferase reporter activity of CH310T1/2 cells transfected with SMO-WT (black squares) or SMO-D473V (grey triangles) following a dose response of GDC-0449. SMO-D473V is partially resistant to this HPI with an approximately 20-fold higher $IC_{50}$. (C) relative cell surface expression of several SMO-D473 mutants.

Figure 19:
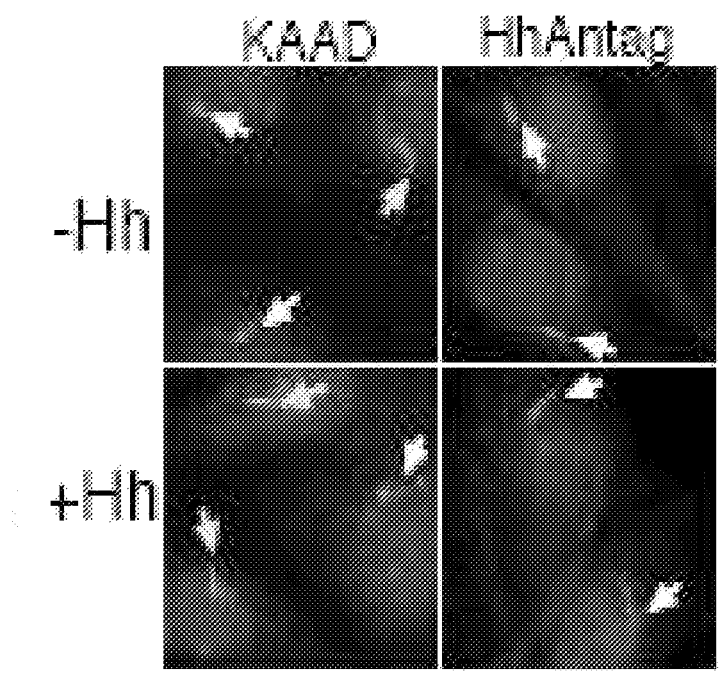

FIG. 19 shows Smo localization in S12 cells treated with either KAAD Cyclopamine or HhAntag in the absence or presence of Shh. As in FIG. 15C, but with other compounds.

Figure 20:
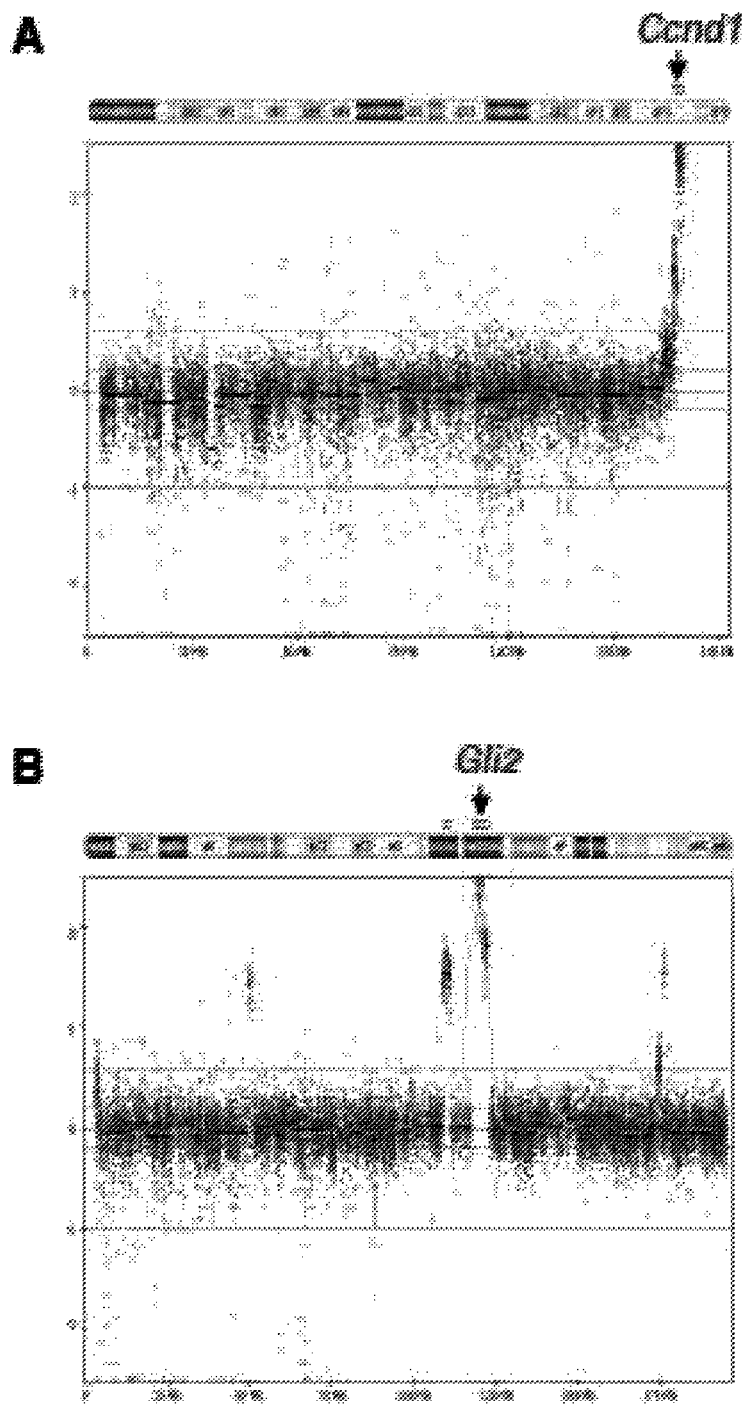

FIG. 20 shows a summary of copy number variations across (A) chromosome 7 in model SG102 and (B) chromosome 1 in model SG152. Log 2 ratio is plotted on the y-axis and chromosomal location is plotted on the x-axis, in relationship to the ideogram. Outer top and bottom lines indicate pre-defined thresholds as described in Materials and Methods.

DETAILED DESCRIPTION

It is a discovery of the present invention that mutational events associated with resistance to chemotherapy for hedgehog-dependent tumors occur in Smoothened (SMO) which impart resistance of the tumors to treatment with compounds that inhibit hedgehog signaling such as cyclopamine and GDC-0449. The present invention provides compositions and methods that are useful as prognostics, diagnostics and therapeutics for cancer that is dependent on Hedgehog signaling.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3rd. edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: *A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); Immunobiology (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993). Cited references are incorporated by reference in their entirety.

I. DEFINITIONS

For purposes of interpreting this specification, the following definitions will apply and whenever appropriate, terms used in the singular will also include the plural and vice versa.

In the event that any definition set forth below conflicts with any document incorporated herein by reference, the definition set forth below shall control.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34):12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816, 567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Bio-* chem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody," as used herein, is an antibody which partially or fully mimics at least one of the functional activities of a polypeptide of interest.

"Growth inhibitory" antibodies are those that prevent or reduce proliferation of a cell expressing an antigen to which the antibody binds. For example, the antibody may prevent or reduce proliferation of cancer cells that express Smo or mutant in vitro and/or in vivo.

Antibodies that "induce apoptosis" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Purified" means that a molecule is present in a sample at a concentration of at least 95% by weight, or at least 98% by weight of the sample in which it is contained.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromosomally or at a chromosomal location that is different from its natural chromosomal location.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "Smo," or "SMO" as used herein, refers to any native SMO from any vertebrate source, including mammals such as primates (e.g. humans) and rodents (e.g., mice and rats), unless otherwise indicated. The term encompasses "full-length," unprocessed SMO as well as any form of SMO that results from processing in the cell. The term also encompasses naturally occurring variants of SMO, e.g., splice variants or allelic variants. "Mutant Smo" as used herein refers to SMO having a mutation in the carboxy-terminal portion of transmembrane 6 of SMO at position 473 of human SMO.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder or to slow the progression of a disease or disorder.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "pharmaceutical formulation" refers to a preparation which is in such form as to permit the biological activity of the active ingredient to be effective, and which contains no additional components which are unacceptably toxic to a subject to which the formulation would be administered. Such formulations may be sterile.

A "sterile" formulation is aseptic or free from all living microorganisms and their spores.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount. The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Nicolaou et al., *Angew. Chem. Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bc1-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyl-transferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell (such as a cell expressing SMO) either in vitro or in vivo. Thus, the growth inhibitory agent may be one which significantly reduces the percentage of cells (such as a cell expressing SMO) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

A "mutant Smo antagonist" is a compound that inhibits the biological activity of a SMO having an amino acid substitution at position 473 of human SMO that changes the wild-type aspartic acid at this position to any other amino acid. The biological activity of SMO is the ability to transducer a signal upon stimulation with hedgehog to activation of Gli transcription factor.

I. Nucleic Acids

The nucleic acids of the invention include isolated mutant SMO-encoding sequences. The nucleic acids comprise a sequence that is at least 80% identical to the nucleic acid sequence of SEQ ID NO:3 and which contain at least one mutation from this sequence to encode any amino acid at position 473 other than aspartic acid (D). In some embodiments, the nucleic acid encodes a histidine (H), glycine (G), phenylalanine (F), tyrosine (Y), leucine (L), isoleucine (I), proline (P), serine (S), threonine (T), methionine (M), glutamine (Q), or asparagine (N) at position 473. In some embodiments, the nucleic acid has at least one mutation from the parental wild-type SMO at nucleotide 1417, 1418 and/or 1419. In some embodiments, the percent identity is 85%, 86%, 87%, 88%, 89%, 90%, 91%, 92%, 93%, 94%, 95%, 96%, 97%, 98%, 99% or 100% with SEQ ID NO:3 providing that there is at least one mutation at position 1417, 1418 and/or 1419. The invention also contemplates fragments of such nucleic acids that span the region of the mutations described above in fragments that are at least 20 nucleotides in length. In some embodiments, the nucleotide fragments are 25, 30, 35, 40, 45, 50, 55, 60, 65, 70, 75, 80, 85, 90, 95, or 100 nucleotides in length. The fragments may be any length that spans the region of the mutations described above up to the full length mutant SMO-encoding nucleic acid molecule. Isolated mutant SMO and fragments thereof may be used, for example, for hybridization, to generate primers and probes for the prognostic and diagnostic assays of the invention, and for expression in recombinant systems (such as to generate mutant SMO protein or portions thereof for use as immunogens and for use in assays of the invention as described herein).

The invention provides nucleic acid probes which may be used to identify the mutant SMO nucleic acid molecule in the methods of the invention. Nucleic acid samples derived from tissue suspected of having a mutant SMO or from tissue wherein the status of SMO is unknown may be screened using a specific probe for mutant SMO using standard procedures, such as described in Sambrook et al., MOLECULAR CLONING: A LABORATORY MANUAL, Cold Spring Harbor Laboratory Press, NY, 1989). Alternatively, the nucleic acid encoding SMO may be amplified from the tissue and probed with a specific probe of the invention to determine the presence of absence of mutant SMO. PCR methodology is well known in the art (Sambrook et al., supra; Dieffenbach et al., PCR PRIMER: A LABORATORY MANUAL, Cold Spring Harbor Laboratory Press, NY, 1995).

Nucleotide sequences (or their complement) encoding mutant SMO have various applications in the art of molecular biology, including uses as hybridization probes, and in the generation of anti-sense RNA and DNA probes. Mutant SMO-encoding nucleic acid will also be useful for the preparation of mutant SMO polypeptides by the recombinant techniques described herein, wherein those mutant SMO polypeptides may find use, for example, in the preparation of anti-mutant SMO antibodies as described herein.

The full-length mutant SMO nucleic acids, or portions thereof, may be used as hybridization probes for identifying mutant SMO.

Optionally, the length of the probes will be about 20 to about 50 bases. The hybridization probes may be derived from at least the mutant region of the full length mutant SNO nucleotide sequence.

By way of example, a screening method will comprise isolating the coding region of mutant SMO using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the mutant SMO gene of the present invention can be used to screen libraries of human cDNA, genomic DNA or mRNA to determine which members of such libraries the probe hybridizes to. Hybridization products may be resolved on polyacrylamide gels. In addition, the SMO mutations may be determined using the method described in the Examples. Hybridization conditions, including moderate stringency and high stringency, are provided in Sambrook et al., supra.

Sequences identified in such library screening methods can be compared and aligned to the known sequences for SMO and mutant SMO. Sequence identity at the carboxy-terminal region of transmembrane domain 6 can be determined using methods known in the art.

Other useful fragments of the SMO-encoding nucleic acids include antisense or sense oligonucleotides comprising a single-stranded nucleic acid sequence (either RNA or DNA) capable of binding to target mutant SMO mRNA (sense) or mutant SMO DNA (antisense) sequences. Antisense or sense oligonucleotides, according to the present invention, comprise a fragment of the coding region of mutant SMO DNA containing the mutation region. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (1988) *Cancer Res.* 48:2659 and van der Krol et al. (1988) *BioTechniques* 6:958.

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of mutant SMO proteins, wherein those mutant SMO proteins may play a role in the resistance of cancer in mammals to chemotherapeutics such as GDC-0449. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Specific examples of preferred antisense compounds useful for inhibiting expression of mutant SMO proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of such oligonucleosides include, but are not limited to: U.S. Pat. Nos. 5,034,506; 5,166,315; 5,185, 444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. (1991) *Science* 254:1497-1500.

Preferred antisense oligonucleotides incorporate phosphorothioate backbones and/or heteroatom backbones, and in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester backbone is represented as —O—P—O—CH$_2$—) described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH2)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred antisense oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al. (1995) *Helv. Chim. Acta* 78:486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$).

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH3), 2'-aminopropoxy (2'-OCH$_2$CH$_2$CH$_2$NH$_2$), 2'-allyl (2'-CH$_2$—CH=CH$_2$), 2'-O-allyl (2'-β-CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$ or —CH$_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in THE CONCISE ENCYCLOPEDIA OF POLYMER SCIENCE AND ENGINEERING, Kroschwitz, J. I., ed., John Wiley & Sons, 1990, pp. 858-859, and those disclosed by Englisch et al., ANGEWANDTE CHEMIE, INTERNATIONAL EDITION, Wiley-VCH, Germany, 1991, 30:613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al. ANTISENSE RESEARCH AND APPLICATIONS, CRC Press, Boca Raton, 1993, pp. 276-278) and are preferred base substitutions, even more particularly when combined with 2'-O-methoxyethyl sugar modifications. Representative U.S. patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al. (1989) *Proc. Natl. Acad. Sci. USA* 86:6553-6556), cholic acid (Manoharan et al. (1994) *Bioorg. Med. Chem. Lett.* 4:1053-1060), a thioether, e.g., hexyl-5-tritylthiol (Manoharan et al. (1992) *Ann. N.Y. Acad. Sci.* 660: 306-309; Manoharan et al. (1993) *Bioorg. Med. Chem. Lett.* 3:2765-2770), a thiocholesterol (Oberhauser et al. (1992) *Nucl. Acids Res.* 20:533-538), an aliphatic chain, e.g., dodecandiol or undecyl residues (Saison-Behmoaras et al. (1991) *EMBO J.* 10:1111-1118; Kabanov et al. (1990) *FEBS Lett.* 259:327-330; Svinarchuk et al. (1993) *Biochimie* 75:49-54, a phospholipid, e.g., di-hexadecyl-rac-glycerol or triethyl-ammonium 1,2-di-O-hexadecyl-rac-glycero-3-H-phosphonate (Manoharan et al. (1995) *Tetrahedron Lett.* 36:3651-3654; Shea et al. (1990) *Nucl. Acids Res.* 18:3777-3783), a polyamine or a polyethylene glycol chain (Manoharan et al. (1995) *Nucleosides & Nucleotides* 14:969-973), or adamantane acetic acid (Manoharan et al. (1995) *Tetrahedron Lett.* 36:3651-3654), a palmityl moiety (Mishra et al. (1995) *Biochim. Biophys. Acta* 1264:229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941 and 6,656,730, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—$(CH_2)_2$—O—$CH_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increase affinity of the oligonucleotide for a target nucleic acid sequence, such as poly-(L-lysine).

Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

Nucleotide sequences encoding a mutant SMO can also be used to construct hybridization probes for mapping the gene which encodes that SMO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

A potential mutant SMO antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example nucleic acids encoding mutant SMO herein, are used to design an antisense RNA oligonucleotide of from about 10 to 40 base pairs in length. A DNA oligonucleotide is designed to be complementary to a region of the gene involved in transcription (triple helix—see Lee et al. (1979) *Nucl. Acids Res.* 6:3073; Cooney et al. (1988) *Science* 241:456; Dervan et al. (1991) *Science* 251:1360), thereby preventing transcription and the production of mutant SMO. The antisense RNA oligonucleotide hybridizes to the mRNA in vivo and blocks translation of the mRNA molecule into the mutant SMO (Okano (1991) *Neurochem.* 56:560); OLIGODE-OXYNUCLEOTIDES AS ANTISENSE INHIBITORS OF GENE EXPRESSION, CRC Press, Boca Raton, Fla., 1988). The oligonucleotides described above can also be delivered to cells such that the antisense RNA or DNA may be expressed in vivo to inhibit production of the mutant SMO. When antisense DNA is used, oligodeoxyribonucleotides derived from the translation-initiation site, e.g., between about −10 and +10 positions of the target gene nucleotide sequence, are preferred.

Potential antagonists of mutant SMO include small molecules that bind to the site occupied in wild-type SMO by GDC-0449, thereby blocking the biological activity of mutant SMO. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi (1994) *Current Biology*, 4:469-471, and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art. Examples of the small molecules that may be used as mutant SMO antagonists are compounds having the following structural formulas:

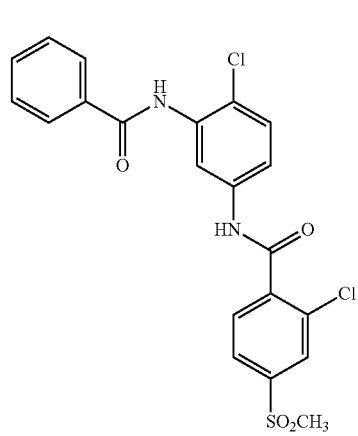

Formula I

-continued

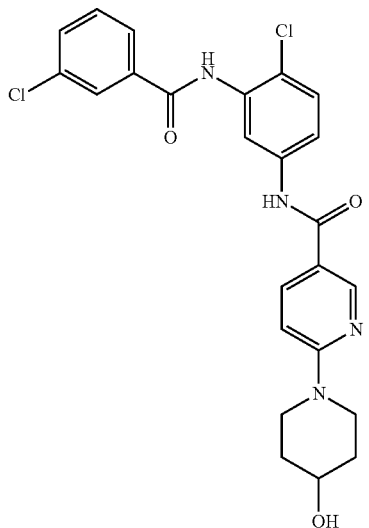

Formula II

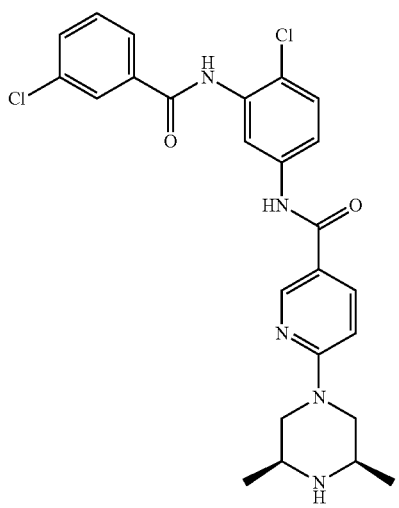

Formula III

II. Proteins

The invention provides isolated mutant SMO proteins. Wild-type human SMO is shown in SEQ ID NO: 1. Mutant human SMO is shown in SEQ ID NO:2 wherein amino acid 473 is shown as "X" which, with respect to this application stands for any amino acid other than aspartic acid (D). In some embodiments, the X is histidine (H), glycine (G), phenylalanine (F), tyrosine (Y), leucine (L), isoleucine (I), proline (P), serine (S), threonine (T), methionine (M), glutamine (Q), or asparagine (N). Mutant SMO and fragments thereof may be produced in recombinant systems as is well known in the art using the mutant SMO nucleic acids described herein. Such nucleic acids may be incorporated into expression vectors as are well-known in that art and transfected into host cells, which may be prokaryotic or eukaryotic cells depending on the proposed use of the protein. Full length or fragments of mutant SMO (in which the fragments contain at least the carboxy-terminal portion of transmembrane domain 6 and amino acid 473 of SEQ ID NO:2) may be used as immunogens to produce antibodies of the invention, or to purify antibodies of the invention, for example.

III. Antibodies

A. Anti-Mutant SMO Antibodies

In one aspect, the invention provides antibodies that bind to SMO, particularly mutant SMO. In one embodiment, an anti-SMO antibody is a monoclonal antibody. In one embodiment, an anti-SMO antibody is an antibody fragment, e.g., a Fab, Fab'-SH, Fv, scFv, or (Fab')₂ fragment. In one embodiment, an anti-mutant SMO antibody is a chimeric, humanized, or human antibody. In one embodiment, an anti-SMO antibody is purified. In certain embodiments, a composition is a pharmaceutical formulation for the treatment of cancer.

1. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')₂ fragments (Carter et al., *Bio/Technology* 10:163-167 (1992)). According to another approach, F(ab')₂ fragments can be isolated directly from recombinant host cell culture. Fab and F(ab')₂ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

2. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA,* 89:4285; Presta et al. (1993) *J. Immunol.,* 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

3. Human Antibodies

Human antibodies of the invention can be constructed by combining Fv clone variable domain sequence(s) selected from human-derived phage display libraries with known human constant domain sequence(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90: 2551 (1993); Jakobovits et al., *Nature,* 362: 255 (1993); Bruggermann et al., *Year in Immunol.,* 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

4. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for SMO and the other is for any other antigen. In certain embodiments, bispecific antibodies may bind to two different epitopes of SMO. Bispecific antibodies may also be used to localize cytotoxic agents to cells which express SMO. These antibodies possess a SMO-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature,* 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The interface comprises at least a part of the $C_H 3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab)$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

5. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

6. Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

7. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) TIBTECH 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336: 1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). Non-limiting examples of in vitro assays to assess ADCC activity of a molecule of interest is described in U.S. Pat. No. 5,500,362 (see, e.g. Hellstrom, I., et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S, and M. J. Glennie, *Blood* 103:2738-2743 (2004)). FcRn binding and in vivo clearance/half life determinations can also be performed using methods known in the art (see, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes. Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |

TABLE 1-continued

| Original Residue | Exemplary Substitutions | Preferred Substitutions |
|---|---|---|
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter, Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region.

8. Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Certain Methods of Making Antibodies

1. Certain Hybridom α-Based Methods

Monoclonal antibodies of the invention can be made using the hybridoma method first described by Kohler et al., *Nature,* 256:495 (1975), and further described, e.g., in Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue,* 26(4):265-268 (2006) regarding human-human hybridomas.

Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology,* 20(3):927-937 (2005) and Vollmers and Brandlein,

*Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide comprising mutant SMO or a fragment thereof, and an adjuvant, such as monophosphoryl lipid A (MPL)/trehalose dicrynomycolate (TDM) (Ribi Immunochem. Research, Inc., Hamilton, Mont.). A polypeptide comprising mutant SMO or a fragment thereof may be prepared using methods well known in the art, such as recombinant methods, some of which are further described herein. Serum from immunized animals is assayed for anti-mutant SMO antibodies, and booster immunizations are optionally administered. Lymphocytes from animals producing anti-mutant SMO antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to mutant SMO. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

2. Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., J. Mol. Biol. (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-mutant SMO clones is desired, the subject is immunized with mutant SMO to generate an antibody response, and spleen cells and/or circulating B cells other peripheral blood lymphocytes (PBLs) are recovered for library construction. In a preferred embodiment, a human antibody gene fragment library biased in favor of anti-mutant SMO clones is obtained by generating an anti-mutant SMO antibody response in transgenic mice carrying a functional human immunoglobulin gene array (and lacking a functional endogenous antibody production system) such that mutant SMO immunization gives rise to B cells producing human antibodies against mutant SMO. The generation of human antibody-producing transgenic mice is described below.

Additional enrichment for anti-mutant SMO reactive cell populations can be obtained by using a suitable screening procedure to isolate B cells expressing mutant SMO-specific membrane bound antibody, e.g., by cell separation using mutant SMO affinity chromatography or adsorption of cells to fluorochrome-labeled mutant SMO followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which mutant SMO is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (*USA*), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci.* (*USA*), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc. Natl. Acad. Sci. USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities of about $10^{-9}$ M or less.

Screening of the libraries can be accomplished by various techniques known in the art. For example, mutant SMO can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized mutant SMO under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA*, 88: 7978-7982 (1991), or by alkali, e.g. as described in Marks et al., *J. Mol. Biol.*, 222: 581-597 (1991), or by mutant SMO antigen competition, e.g. in a procedure similar to the antigen competition method of Clackson et al., *Nature*, 352: 624-628 (1991). Phages can be enriched 20-1.000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for mutant SMO. However, random mutation of a selected antibody (e.g. as performed in some affinity maturation techniques) is likely to give rise to many mutants, most binding to antigen, and a few with higher affinity. With limiting mutant SMO, rare high affinity phage could be competed out. To retain all higher affinity mutants, phages can be incubated with excess biotinylated mutant SMO, but with the biotinylated mutant SMO at a concentration of lower molarity than the target molar affinity constant for mutant SMO. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-mutant SMO clones may be selected based on activity. In certain embodiments, the invention provides anti-mutant SMO antibodies that bind to living cells that naturally express mutant SMO, such as GDC-0449-resistant tumor cells. In one embodiment, the invention provides anti-mutant SMO antibodies that bind to the same region as that bound by GDC-0449 in wild type SMO. Fv clones corresponding to such anti-mutant SMO antibodies can be selected by (1) isolating anti-mutant SMO clones from a phage library as described above, and optionally amplifying the isolated population of phage clones by growing up the population in a suitable bacterial host; (2) selecting mutant SMO and a second protein against which blocking and non-blocking activity, respectively, is desired; (3) adsorbing the anti-mutant SMO phage clones to immobilized mutant SMO; (4) using an excess of the second protein to elute any undesired clones that recognize mutant SMO-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-mutant SMO antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

3. Vectors, Host Cells, and Recombinant Methods

Antibodies may also be produced using recombinant methods. For recombinant production of an anti-mutant SMO antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

c) Selection Gene Component Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, duckweed (Lemnaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCINT™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical are well-established in the art, consistent with the above-described methodologies and/or as deemed appropriate by one skilled in the art for a particular antibody of interest.

C. Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) *Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) *Adv. Drug Deliv. Rev.* 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., *Lancet* (Mar. 15, 1986) pp. 603-05; Thorpe (1985) "Antibody Carriers Of Cytotoxic Agents In Cancer Therapy: A Review," in *Monoclonal Antibodies '84: Biological And Clinical Applications* (A. Pinchera et al., eds) pp. 475-506. Both polyclonal antibodies and monoclonal antibodies have been reported as useful in these strategies (Rowland et al., (1986) *Cancer Immunol. Immunother.* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al (1998) *Cancer Res.* 58:2928; Hinman et al (1993) *Cancer Res.* 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) *Eur. Jour. Nucl. Med.* 27(7):766-77; Wiseman et al (2002) *Blood* 99(12):4336-42; Witzig et al (2002) *J. Clin. Oncol.* 20(10):2453-63; Witzig et al (2002) *J. Clin. Oncol.* 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (*Drugs of the Future* (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) *Nature Biotechnol.* 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC 1065, and the derivatives of these toxins that have toxin activity, are also contemplated herein.

1. Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

2. Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983, 340, filed Nov. 5, 2004, hereby incorporated by reference in its entirety (disclosing, e.g., linkers and methods of preparing monomethylvaline compounds such as MMAE and MMAF conjugated to linkers).

3. Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma 1I$, $\alpha 2I$, $\alpha 3I$, N-acetyl-$\gamma 1I$, PSAG and $\theta I1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

4. Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

5. Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

IV. Methods

A. Diagnostic Methods and Methods of Detection of Mutant SMO with Antibodies

In one aspect, antibodies of the invention are useful for detecting the presence of mutant SMO in a biological sample. The term "detecting" as used herein encompasses quantitative or qualitative detection. In certain embodiments, a biological sample comprises a cell or tissue, such as tumor tissue.

In one aspect, the invention provides a method of detecting the presence of mutant SMO in a biological sample. In certain embodiments, the method comprises contacting the biological sample with an anti-mutant SMO antibody under conditions permissive for binding of the anti-mutant SMO antibody to mutant SMO, and detecting whether a complex is formed between the anti-mutant SMO antibody and mutant SMO.

In one aspect, the invention provides a method of diagnosing a disorder associated with expression of mutant SMO. In certain embodiments, the method comprises contacting a test cell with an anti-mutant SMO antibody; determining the level of expression (either quantitatively or qualitatively) of mutant SMO by the test cell by detecting binding of the anti-mutant SMO antibody to mutant SMO; and comparing the level of expression of mutant SMO by the test cell with the level of expression of mutant SMO by a control cell (e.g., a normal cell of the same tissue origin as the test cell or a cell that expresses wild-type SMO at levels comparable to such a normal cell), wherein a higher level of expression of mutant SMO by the test cell as compared to the control cell indicates the presence of a disorder associated with increased expression of mutant SMO. In certain embodiments, the test cell is obtained from an individual suspected of having a disorder associated with increased expression of mutant SMO. In certain embodiments, the disorder is a cell proliferative disorder, such as a cancer or a tumor.

Exemplary disorders that may be diagnosed using an antibody of the invention include, but are not limited to medulloblastoma, pancreatic cancer basal cell carcinoma.

Certain other methods can be used to detect binding of antibodies to mutant SMO. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, antibodies are immobilized on an insoluble matrix. Immobilization may entail separating an anti-mutant SMO antibody from any mutant SMO that remains free in solution. This conventionally is accomplished by either insolubilizing the anti-mutant SMO antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-mutant SMO antibody after formation of a complex between the anti-mutant SMO antibody and mutant SMO, e.g., by immunoprecipitation.

It is understood that any of the above embodiments of diagnosis or detection may be carried out using an immunoconjugate of the invention in place of or in addition to an anti-mutant SMO antibody.

B. Methods of Detecting Mutant SMO with Nucleic Acid Probes

In one aspect, nucleic acid probes as described herein are useful for detecting the presence of mutant SMO nucleic acid in a biological sample. The term "detecting" as used herein encompasses quantitative or qualitative detection. In certain embodiments, a biological sample comprises a cell or tissue, such as tumor tissue.

In one aspect, the invention provides a method of detecting the presence of mutant SMO-encoding nucleic acid in a biological sample. In certain embodiments, the method comprises contacting nucleic acid from the biological sample with a probe as described herein and hybridizing the probe to the nucleic acid under conditions permissive for hybridization under stringent conditions, and detecting whether a complex is formed between the probe and the nucleic acid sample.

The mutant SMO-encoding nucleic acid may be detected using any methodology known in the art including, but not limited to the use of probes as described herein, or by PCR amplification, rtPCR sequencing, single strand conformational polymorphism (SSCP), differential restriction digestion of DNA, hybridization, or any other method known in the art.

In these methods, detection of a mutant SMO as described herein cell indicates the presence of a disorder associated with increased expression of mutant SMO (i.e., resistance to treatment with a Smo inhibitor such as GDC-0449). In certain embodiments, the test cell is obtained from an individual suspected of having a resistant tumor associated with expression of mutant SMO.

Exemplary disorders that may be diagnosed using an antibody of the invention include, but are not limited to medulloblastoma, pancreatic cancer basal cell carcinoma.

C. Methods of Detecting Mutant SMO in Cell Based Assays

Mutant SMO may be detected in cell based assays as known in the art including, but not limited to binding of a mutant SMO-detecting antibody to the surface of a cell sample, such as a tumor sample in vitro Immunohistochemical staining of histological preparations of tumor samples or tissue suspected of containing mutant SMO. Functional assays in which a tissue sample is contacted with GDC-0449 and hedgehog to determine whether Hh signaling occurs (e.g., by measuring activation of pathway components, expression of Gli, and the like). Any functional assay using the Hh signaling pathway that can be disrupted using GDC-0449 may be used in the method of the invention to determine the presence of a mutant SMO.

D. Methods of Screening for Compounds that Bind to Mutant SMO

The invention provides a method for screening for compounds that bind to mutant SMO. Without being held to any particular mode of operation, it is expected that much in the way that GDC-0449 binds wild-type SMO and doesn't bind mutant SMO, a compound which acts as an inhibitor of mutant SMO would dind mutant SMO in the same region within the carboxy-terminal portion of the transmembrane domain NO. 6 (TM6). Thus, one may express this region of the mutant SMO protein and run binding assays using a library of compounds by any means known in the art. Also one may use a smaller library of compounds represented by variations of GDC-0449 using a modeling approach based on potential contact points of GDC-0449 and then modeling similar contact points for mutant SMO and variations of GDC-0449. Such modeling programs and algorithms may be any that are known in the art. Compounds that bind mutant SMO and wild-type SMO may be identified that are inhibitors of both wild-type and mutant SMO. Alternatively, compounds may be discovered that bind to mutant SMO, but which do not bind to wild-type SMo and therefore are inhibitors only for mutant SMO.

In one embodiment, the compounds to be screened are small molecule compounds such as variants of GDC-0449. In other embodiments, the compounds that bind mutant SMO are antibodies that specifically recognize an epitope that is in the same region as the binding site of GDC-0449 to wild-type SMO. In one embodiment the antibody binds to a region in the carboxy-terminal portion of TM6 of mutant SMO and inhibits mutant SMO activity.

Compounds may alternatively, or additionally be screened for their ability to inhibit mutant SMO activity. In these embodiments, one may assess the ability of these compounds to inhibit hedgehog signaling in cells expressing mutant SMO. These assays may be performed in cells that have a hedgehog signaling pathway intact but which express a recombinant SMO bearing the mutation in place of, or in addition to wild-type SMO. In these assays one determines the ability of the cell to have active hedgehog signaling when incubated with hedgehog in the presence or ansence of the candidate inhibitor. If hedgehog signaling is inhibited in the presence of the candidate compound, such compound is a hedgehog inhibitor. In some embodiments the cells express both wild-type and mutant SMO and are incubated with GDC-0449 and a candidiate inhibitor. In other embodiments, the cells express only mutant SMo and may be incubated with Hh and the candidate inhibitor alone (i.e., in the absence of GDC-0449). The compound is an inhibitor of mutant SMO if Hh signaling is reduced or inhibited in such cells.

E. Therapeutic Methods Using Compounds that Bind Mutant SMO

The invention provides methods of treating a patient in having a hedgehog signaling-dependent tumor that is resistant to chemotherapeutic compounds such as GDC-0449 with a compound that binds a mutant SMO.

1. Therapeutic Methods

An antibody of the invention may be used in, for example, in vitro, ex vivo, and in vivo therapeutic methods. In one aspect, the invention provides methods for treating cancer, inhibiting unwanted cellular proliferation, inhibiting metastasis of cancer and inducing apoptosis of tumor cells either in vivo or in vitro, the method comprising exposing a cell to an antibody of the invention under conditions permissive for binding of the antibody to mutant SMO. In certain embodiments, the cell is a myelogenous leukemia cell, a lung cancer cell, a gastric cancer cell, a breast cancer cell, a prostate cancer cell, a renal cell cancer cell, and a glioblastoma cell. In one embodiment, an antibody of the invention can be used for inhibiting an activity of mutant SMO, the method comprising exposing mutant SMO to an antibody of the invention such that the activity of mutant SMO is inhibited.

In one aspect, the invention provides methods for treating cancer comprising administering to an individual an effective amount of an antibody of the invention. In certain embodiments, a method for treating cancer comprises administering to an individual an effective amount of a pharmaceutical formulation comprising an antibody of the invention and, optionally, at least one additional therapeutic agent, such as those provided below.

Antibodies of the invention can be used either alone or in combination with other compositions in a therapy. For instance, an antibody of the invention may be co-administered with at least one additional therapeutic agent and/or adjuvant. In certain embodiments, an additional therapeutic agent is an anti-VEGF antibody.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

In one embodiment, an antibody of the invention is used in a method for binding mutant SMO in an individual suffering from a disorder associated with increased mutant SMO expression and/or activity, the method comprising administering to the individual the antibody such that mutant SMO in the individual is bound. In one embodiment, the mutant SMO is human mutant SMO, and the individual is human.

An antibody of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described, e.g., in Marasco, *Gene Therapy* 4: 11-15 (1997); Kontermann, *Methods* 34: 163-170 (2004); U.S. Pat. Nos. 6,004,940 and 6,329,173; U.S. Patent Application Publication No. 2003/0104402, and PCT Publication No. WO2003/077945. See also, for example, WO96/07321 published Mar. 14, 1996, concerning the use of gene therapy to generate intracellular antibodies.

Intracellular expression of an intrabody may be effected by introducing a nucleic acid encoding the desired antibody or antigen-binding portion thereof (lacking the wild-type leader sequence and secretory signals normally associated with the gene encoding that antibody or antigen-binding fragment) into a target cell. One or more nucleic acids encoding all or a portion of an antibody of the invention can be delivered to a target cell, such that one or more intrabodies are expressed which are capable of binding to an intracellular target polypeptide and modulating the activity of the target polypeptide. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

In certain embodiments, nucleic acid (optionally contained in a vector) may be introduced into a patient's cells by in vivo and ex vivo methods. In one example of in vivo delivery, nucleic acid is injected directly into the patient, e.g., at the site where therapeutic intervention is required. In a further example of in vivo delivery, nucleic acid is introduced into a cell using transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of certain gene marking and gene therapy protocols, see Anderson et al., *Science* 256:808-813 (1992), and WO 93/25673 and the references cited therein. In an example of ex vivo treatment, a patient's cells are removed, nucleic acid is introduced into those isolated cells, and the modified cells are administered to the patient either directly or, for example, encapsulated within porous membranes which are implanted into the patient (see, e.g., U.S. Pat. Nos. 4,892,538 and 5,283, 187). A commonly used vector for ex vivo delivery of a nucleic acid is a retroviral vector.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

Entry of antibodies into target cells can be enhanced by other methods known in the art. For example, certain sequences, such as those derived from HIV Tat or the Antennapedia homeodomain protein are able to direct efficient uptake of heterologous proteins across cell membranes. See, e.g., Chen et al., *Proc. Natl. Acad. Sci. USA* (1999), 96:4325-4329.

When the binding target of an antibody is located in the brain, certain embodiments of the invention provide for the antibody to traverse the blood-brain barrier. Several art-known approaches exist for transporting molecules across the blood-brain barrier, including, but not limited to, physical methods, lipid-based methods, stem cell-based methods, and receptor and channel-based methods.

Physical methods of transporting an antibody across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., *Gene Therapy* 9: 398-406 (2002)), interstitial infusion/convection-enhanced delivery (see, e.g., Bobo et al., *Proc. Natl. Acad. Sci. USA* 91: 2076-2080 (1994)), and implanting a delivery device in the brain (see, e.g., Gill et al., *Nature Med.* 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989)), permeabilization by, e.g., bradykinin or permeabilizer A-7 (see, e.g., U.S. Pat. Nos. 5,112,596, 5,268, 164, 5,506,206, and 5,686,416), and transfection of neurons that straddle the blood-brain barrier with vectors containing genes encoding the antibody (see, e.g., U.S. Patent Publication No. 2003/0083299).

Lipid-based methods of transporting an antibody across the blood-brain barrier include, but are not limited to, encapsulating the antibody in liposomes that are coupled to antibody binding fragments that bind to receptors on the vascular endothelium of the blood-brain barrier (see, e.g., U.S. Patent Application Publication No. 20020025313), and coating the antibody in low-density lipoprotein particles (see, e.g., U.S. Patent Application Publication No. 20040204354) or apolipoprotein E (see, e.g., U.S. Patent Application Publication No. 20040131692).

Stem-cell based methods of transporting an antibody across the blood-brain barrier entail genetically engineering neural progenitor cells (NPCs) to express the antibody of interest and then implanting the stem cells into the brain of the individual to be treated. See Behrstock et al. (2005) *Gene Ther.* 15 Dec. 2005 advanced online publication (reporting that NPCs genetically engineered to express the neurotrophic factor GDNF reduced symptoms of Parkinson disease when implanted into the brains of rodent and primate models).

Receptor and channel-based methods of transporting an antibody across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above therapeutic methods may be carried out using an immunoconjugate of the invention in place of or in addition to an anti-mutant SMO antibody.

Compounds for Treating GDC-0449-Resistant Tumors

Among the small molecule compounds that may be used to treat GDC-0449-resistant tumors due to a mutation in smoothened at amino acid position 473 are the following:

Formula I

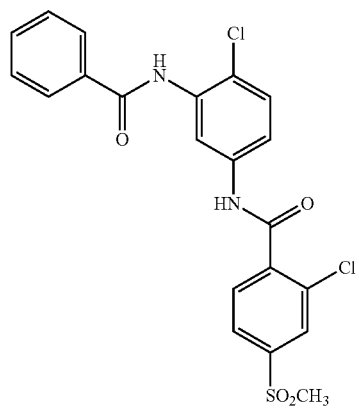

Formula II

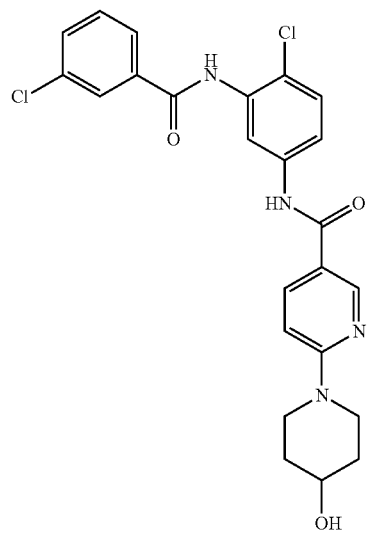

Formula III

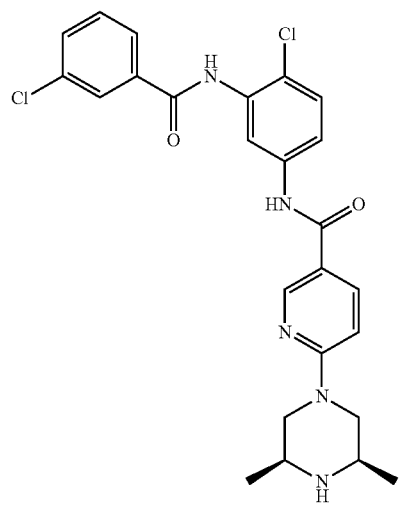

The small molecule is provided in an effective amount to inhibit mutant SMO activity without causing untoward effects on the subject to whom the compound is administered. The compound may be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

The compounds of the invention may further be administered with a PI3K inhibitor. The administration of the PI3K inhibitor prevents or delays further mutagenesis of the SMO protein and acquired resistance to Smo inhibitors. Suitable PI3K inhibitors include any known in the art, including but not limited to those described in Maira S-M et al. (2009) "PI3K Inhibitors for Cancer Treament: Where Do We Stand?" *Biochem. Soc. Trans.* 37:265-272.

EXAMPLES

Introduction

It has recently been demonstrated that treatment of a medulloblastoma patient harboring widespread metastatic disease with the novel Hh pathway inhibitor, GDC-0449, resulted in a dramatic and rapid response to treatment (Charles M. Rudin et al. (2009) *N. Engl. J. Med.* 361:1173-1178). GDC-0449 targets the G protein coupled-like receptor, Smoothened (SMO), which becomes activated following loss of PTCH1 (Charles M. Rudin et al. (2009) *N. Engl. J. Med.* 361:1173-1178; Molckovsky, A. and L. L. Siu (2008) *J. Hematol. Oncol.* 1:20).

Figure 4:
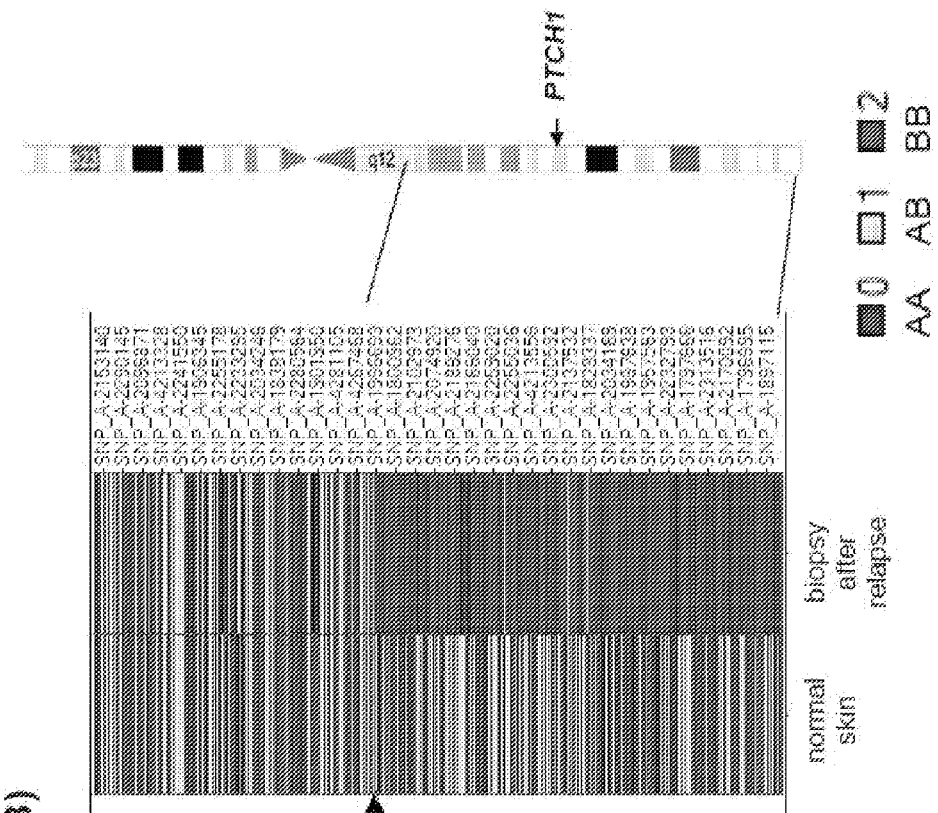
FIG. 4 shows the presence and loss of heterozygosity (LOH) of the pre-existing PTCH1 W844C mutation is confirmed in the biopsy taken at relapse. (A) Nucleotide sequence tracings confirm the pre-existing PTCH1 W844C homozygous mutation in a biopsy taken at relapse. (B) Loss of heterozygosity on chromosome 9 in DNA obtained from the biopsy at relapse, as assessed by AffymetrixSNP arrays. Stretches of homozygous allele calls for each SNP probe across the highlighted region of chromosome 9 are shown.
Figure 4:
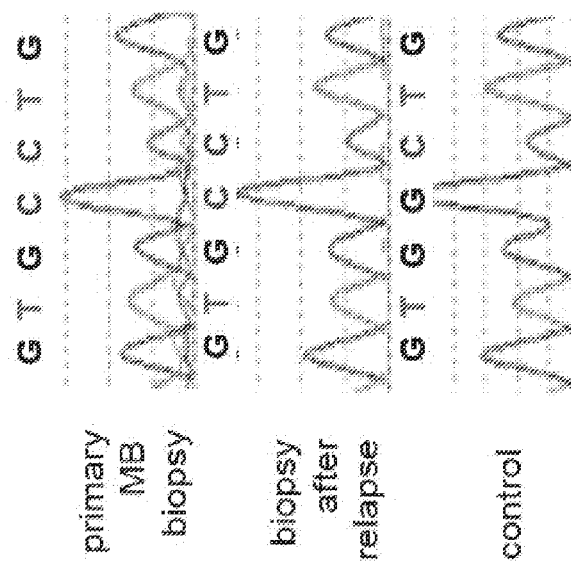
Figure 5:
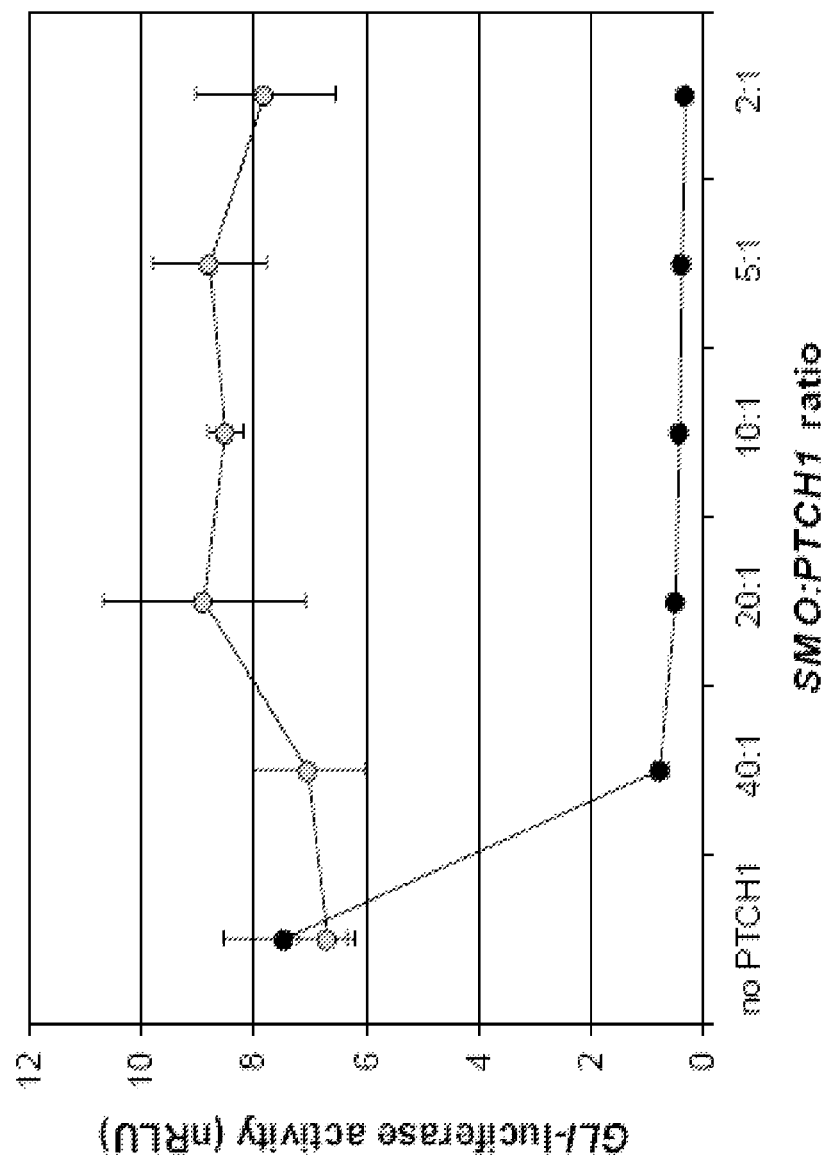
FIG. 5 shows PTCH1-W844C is unable to suppress Hh pathway activity. GLI-luciferase reporter activity following co-transfection of various input ratios of SMO and either WT (closed circles) or W844C (open circles) PTCH1 DNA in C3H10T1/2 cells.

Molecular profiling of this medulloblastoma patient's primary and metastatic tumor taken prior to treatment with GDC-0449 revealed an underlying somatic mutation in PTCH1 (PTCH1-W844C), as well as upregulated expression of Hh pathway target genes, supporting the hypothesis that the tumor was driven by dysregulated Hh signaling (C. M. Rudin et al. (2009) *N. Engl. J. Med.* 361:1173-1178) FIG. 4. The PTCH1-W844C mutation was not capable of suppressing SMO activity in a Hh-responsive, GLI-luciferase reporter cell line (C3H10T1/2 fibroblasts) when co-transfected together with wild-type (WT) SMO, indicating that this specific mutation can inhibit the ability of PTCH1 to repress SMO and thus lead to aberrant, ligand-independent activation of the Hh pathway (FIG. 5). Despite the marked tumor shrinkage initially observed in this patient, PET scans taken ~3 months following initiation of treatment indicated disease progression. A fine needle aspirate of a progressing lesion was obtained for confirmation of disease recurrence, and for subsequent molecular profiling to explore mechanisms of acquired resistance to GDC-0449. Sequencing of PTCH1 confirmed the presence of the previously detected homozygous PTCH1-W844C mutation, accompanied by loss of heterozygosity (FIG. 4).

To characterize the mechanism of relapse, in the present application, we evaluated the status of known components of the Hh pathway including SMO, the direct target of GDC-0449.

Materials and Methods

Reagents and Constructs.

KAAD-Cyclopamine was purchased from Toronto Research Chemicals Inc. (cat. #K171000). GDC-0449 was made at Genentech (A. Molckovsky and L. L. Siu (2008) *J.*

*Hematol. Oncol.* 1:20). All Hh inhibitors were stored as 30 mM stocks in 100% DMSO (Sigma) at −20° C. Human SMO, human PTCH1 (transcript variant 1b, GenBank NM_000264.3) and eGFP were cloned into pRK5 (BD Biosciences) and expressed from the CMV promoter. Point mutations were introduced with the QuikChange II Site-Directed Mutagenesis Kit from Stratagene (Cat. #200524), and a FLAG tag was introduced at the carboxy termini of wild-type and mutant human SMO by PCR using Platinum Taq DNA Polymerase High Fidelity from Invitrogen (Cat. #11304-011) (Murone et al. (1999) *Curr Biol.* 9:76-84) previously described the Hh luciferase reporter Gli-BS and the *Renilla* transfection control plasmid (pRL-TK) are from Promega (Cat. #E2241). All constructs were confirmed by sequencing.

Alanine Scan Mutagenesis.

SMO mutants were generated from pRK5-SMO as described above. Alanines were mutated to leucine (CTG), while all other residues were mutated to alanine (GCA).

Hedgehog Pathway Gene Status.

Exons covering the open reading frame of mouse and human SMO/SMO, in addition to exon 15 of PTCH1, were PCR-amplified from genomic DNA using a pair of nested primers. The internal pair of primers used in the amplification contained m13 forward or m13 reverse primer sequences. After PCR, free nucleotides and excess primer were removed using ExoSAP-IT kit (USB); PCR products were sequenced in both directions using m13 sequencing primers. PCR products were cycle-sequenced using BigTerminator Kit (Applied Biosystems). All sequencing products were resolved on a 3730×1 sequencing machine (Applied Biosystems). Sequence trace files were analyzed using Sequencher (GeneCodes) and/or Mutation Surveyor (SoftGenetics LLC). The SMO D473H mutation was additionally confirmed by primer extension and MALDI-TOF mass spectroscopy of the amplified DNA (MassARRAY, Sequenom, San Diego, Calif.). The following primers were utilized: Extend Primer (UEP.D473H): TCAGCTGCCACTTCTAC (5081.3 Da) (SEQ ID NO:13); Analyte G: TCAGCTGCCACTTCTACG (5368.5 Da) (SEQ ID NO:14); Analyte C: TCAGCTGCCACTTCTACC (5328.5 Da) (SEQ ID NO:15). The SMO D473H mutation was previously reported as a rare SNP (ref SNP ID: rs17710891), however we were unable to confirm this genotype in DNA obtained from the affected individual or their pedigree.

Deep Sequencing.

The region surrounding the SMO exon 8 mutational site was PCR amplified from the primary disease biopsy DNA, metastatic disease biopsy DNA and a control normal DNA (Promega, Wis.), pooled and analyzed on an Illumina Genome Analyzer. A sequence barcode 'AACGCA' for the primary disease DNA, 'AACTGC' for metastatic disease DNA and 'AAGCCT' for normal DNA was added as part of the PCR process and this sequence was used to sort the sequences into the three categories post sequencing. A total of 57 million 36-bp reads covering the target region was analyzed for the presence of the mutated allele (G>C). We successfully aligned 93.5% of the short reads to the target, requiring a perfect match to one of the three sequence barcodes, and allowing for two mismatches after masking the position of the mutant allele. Alignments were performed using MAQ with the default criteria for filtering poor quality alignments (s1). Analysis was restricted to bases having a quality score ≥30, and at each position, the proportion of reads containing variant alleles was computed. The mutant G>C allele of interest occurred in 0.029% of the reads in the primary samples (out of 11.2 million reads with quality ≥30), 0.02% in the metastatic sample (out of 13.7 million reads), and 0.02% in the normal sample (out of 10.2 million reads). Using the barcode region and the sequence outside of the position of interest we estimated the background sequencing error rate to be 0.02%, which represents the threshold of detection using this technology. A binomial test (p~0) excludes the presence of the mutant allele at a 0.1% or higher level in any of the samples.

Luciferase Reporter Assays.

C3H10T1/2 cells (ATCC, Cat. #CCL-226) were seeded into six-well plates at $1.5 \times 10^5$ cells/well in DMEM High Glucose with 4 mM glutamine, 10 mM Hepes pH 7.2 and 10% FBS the afternoon before transfection. Cells were transfected the next morning with 400 ng of expression construct, 400 ng of Gli-BS and 200 ng of pRL-TK per well using GeneJuice Transfection Reagent (Novagen, Cat. #70967). For the PTCH1 inhibition experiments, cells were transfected with an additional 200 ng of DNA containing varying ratios of PTCH1 to eGFP expression constructs. For the NF-KB and SV40 reporter assays, Gli-BS was replaced with either pGL4.32 or pGL3-Promoter. Six hours later, cells were collected by trypsin treatment and each well was redistributed over four wells of a 12-well plate. The FBS content of the culture medium was reduced to 0.5% the following morning to induce formation of primary cilia, and small molecule Hh inhibitors were added at indicated concentrations. Luciferase activity was determined 48 hours later with the Dual-Glo Luciferase Assay System (Promega, Cat. #E2940). Values were divided by *Renilla luciferase* activities to normalize for transfection efficiency and are shown as the mean of three separate experiments±1 standard deviation.

Gli-Luciferase Reporter Assays for D473 Mutants (All Amino Acid Possibilities).

Gli-luciferase reporter assays were performed as described above (Rudin, C. M. et al. (2009) *N. Engl. J. Med.* 361:1173-1178) with the following modifications; C3H10T1/2 cells (ATCC, CCL-226) were seeded into six-well plates at $1.85 \times 10^5$ cells/well and values shown are the mean of four separate experiments±1 standard deviation (SD).

[$^3$H]-GDC-0449-Binding Assays.

HEK-293 cells were transfected with SMO expression constructs, harvested, fixed and washed as previously described. Cells were resuspended in PBS, seeded into 96 well plates ($2 \times 10^6$ cells/well) and incubated for 1 h at 37° C. with 5 nM [$^3$H]-GDC-0449 (0.05 Xi/well; Tritec, Teufen, Switzerland) in the presence or absence of 50 μM unlabeled GDC-0449. Cells were transferred to filter plates (Perkin Elmer #6005174) using a cell harvester (Wallac) and washed 5 times with water. Plates were dried and bound radioactivity was measured using a Topcount scintillation counter and Microscint-20 scintillation cocktail (both from Perkin Elmer). Data were either displayed as raw counts, or were normalized to SMO-WT after subtraction of background values (obtained from untransfected cells).

FACS Analysis of SMO Mutants.

FACS analysis to determine the cell surface expression of SMO mutants was performed as previously described. The percent SMO-positive cells were normalized to SMO-WT controls.

Western Blot for Expression of SMO and Flag in 10T1/2 cells.

10T1/2 cells were transiently transfected using Genejuice Transfection Reagent (Novagen 70967) with either WT SMO, mut SMO, or empty pRK5 vector for 48 hours. Western blot was carried out using standard published methods utilizing a 4-12% Tris-Glycine gel and a nitrocellulose membrane. Protein was detected using the anti-Flag antibody M2 (Sigma F3165) with an Alexa 488 anti-mouse secondary (Molecular Probes A11001). Blots were imaged by fluorescence using an Amersham Biosciences Typhoon Trio. For FACS analysis, transfected cells were dislodged in 1 mM EDTA/PBS and subsequently incubated with SMO antibody, 2D11 (1 ug/ml), followed by 20 min incubations with biotin-SP-conjugated AffiniPure goat anti-mouse IgG (1:100, Jackson Immunoresearch Labs 115-065-071) and R-Phycoerythrin-conjugated Streptavidin (1:50, Jackson Immunoresearch Labs 016-110-084). After resuspension in PI (500 ng/ml), cells were analyzed using a BD Biosciences HTS FacsCalibur.

$^{14}$C-GDC0449 Binding and Competition.

293 cells were transiently transfected using Genejuice with either WT SMO or mut SMO for 48 hours. After harvesting in 1 mM EDTA in PBS, 10 million cells were fixed with 4% PFA for 10 minutes at room temperature, washed 3× with 1 mM EDTA in PBS then incubated for 1 hour at room temperature with 14C-GDC-0449 (5 nM), with or without 50 µM cold GDC-0449. Cells were washed 3× with PBS then transferred to a scintillation vial. 15 ml PicoFluor 40 was added and counts per minute were assessed using a PerkinElmer liquid scintillation analyzer Tri-Carb 2900TR. All samples were done in triplicate.

Generation of Mouse Medulloblastoma Models of GDC-0449 Resistance.

Starting at 4 weeks of age, Ptch1$^{-/+}$; p53$^{-/-}$ mice on a C57BL/6 background were monitored weekly for the presence of medulloblastomas by MRI. All mice were monitored daily for any signs of abnormal behavior indicative of CNS involvement. Mice with well-defined tumors detected by MRI were sacrificed and tumors dissected from normal cerebellum, mechanically dissociated, and 5×10$^6$ cells injected into the lateral thoracic region of CD-1 nude mice (CRL). Tumors were allowed to progress to approximately 400 mm$^3$ in size at which time mice were treated with 75 mg/kg GDC-0449 (free base equivalents) once daily until tumors decreased in size to approximately 100 mm3. Mice were then given a dosing holiday until re-growth occurred. Sequential rounds of treatment and re-growth were applied until the tumors were no longer responsive to daily dosing at which time dosing frequency was increased to twice daily at 75 mg/kg. Resistance developed over a period of 7-10 weeks in these models suggesting that suboptimal dosing of GDC-0449 can rapidly lead to resistance. Tumors that failed to respond to this dose and frequency were then harvested for molecular analysis and passaged (first passage) subcutaneously into additional mice for expansion. In order to analyze pathway modulation in response to GDC-0449, tumor-bearing mice at second-passage were dosed once with 75 mg/kg GDC-0449 and harvested 6 hours post dose for analysis. All mice were housed and maintained according to the animal use guidelines of Genentech, Inc, conforming to California State legal and ethical practices. References for FIG. 4: H. Li, J. Ruan and R. Durbin (2008) *Genome Res.* 18:1851.

Mouse Pharmacokinetic Studies.

Mouse pharmacokinetic studies with compounds 4 and 5 were essentially performed as described for GDC-0449 (Wong H., et al. (2009) *Xenobiotica* 39:850-861). Briefly, 24 female CD-1 mice weighing 25 to 33 g at study initiation were given a single oral 100 mg kg-1 dose of either compound 4 or 5 as a suspension in 0.5% methylcellulose with 0.2% Tween-80 (MCT). Blood samples (n=3 mice per time point) were collected in tubes containing EDTA as an anticoagulent by terminal cardiac puncture under isoflurane at the following time points: 5, 15 and 30 min; and 1, 3, 6, 9 and 24 h post-dose. Blood samples were centrifuged to collect plasma, which was stored at −80° C. until drug concentrations were quantified by LC/MS/MS.

Drug Treatment of Animals with MB Allografts.

Tumor-bearing animals were generated via serial subcutaneous propagation of murine Ptch+/−; p53−/− MB tumor lines (Wetmore C. et al. (2001) *Cancer Res.* 61:513-516). Subcutaneous tumors 1500-2000 mm3 were excised from donor mice under aseptic conditions, minced in High Glucose DMEM by repeated slicing and chopping with two #10 scalpels and passed through a cell dissociation sieve (Sigma, CD1-1KT). The resulting single cell suspension was washed twice in High Glucose DMEM and filtered through a 70 µm nylon cell strainer (BD Falcon) before counting in a Vi-CELL cell viability analyzer (Beckman Coulter). Approximately 2.5–4×106 live cells in a 100 µl volume were injected subcutaneously into the right lateral thorax of 7 to 10-week-old female CD-1 nude mice (CRL). Tumor dimensions were measured with Ultra Cal IV calipers (Fred V. Fowler Company Inc., Newton, Mass.) and tumor volume was calculated using the formula v=0.5×a×b2, where a and b are the shortest and longest perpendicular tumor diameters, respectively. When tumors reached 125-350 mm$^3$ in volume, animals were separated into treatment groups with similarly sized tumors and drug administration was initiated. Compounds were formulated in MCT and mice were administered orally 0.2 ml of either vehicle twice daily, compound 5 at 100 mg kg-1 once daily, or HhAntag at 100 mg kg-1 twice daily for the HPI study, and either vehicle or drug at 8 to 10 mg kg-1 once daily for the PI3K inhibitor study. Mice were euthanized if tumors exceeded 2000 mm$^3$ and/or if their body weight dropped >20%. All mice were housed and maintained according to the animal use guidelines of Genentech Inc., conforming to California State legal and ethical practices.

Statistical Methods.

Fitted tumor growth curves were derived using the non-linear mixed effect package 'nlme', version 3.1-96 (Pinheiro J. et al. (2009) Package 'nlme', version 3.1-96) in R version 2.9.2 (R Development Core Team 2008; R Foundation for Statistical Computing; Vienna, Austria).

RNA Isolation and qRT-PCR.

Total RNA was extracted from tumors using the RNeasy Mini Kit (Qiagen 74106). RNA concentration was determined with a NanoDrop spectrophotometer and qRT-PCR was carried out with 100 ng RNA on an Applied Biosystems 7500 theromocycler. Expression levels were normalized to Rpl119 and are presented as normalized gene expression values (2-ΔCt). A TaqMan gene expression assay for Gli1 was purchased from Applied Biosystems, for which the probe (Assay ID: Mm00494646_g1) spanned the exon 3-4 boundary. The primer and probe sequences for Rpl19 are F: 5'-AGAAGGTGACCTGGATGAGA-3' (SEQ ID NO:10), R: 5'-TGATACATATGGCGGTC AATCT-3' (SEQ ID NO:11) and P: 5'-CTTCTCAGGAGATACCGGGAATC CAAG-3' (SEQ ID NO:12).

Smo Immunostaining.

S12 cells were plated to confluency and serum-starved for 16 h±200 ng/ml octyl-Shh in the presence of saturating compound levels (5 µM for cyclopamine, 104 for the others). Cells were then fixed in 100% methanol, stained with anti-Smo (5928B, a rabbit pAb raised against the C-terminal tail of mouse Smo (Wen X. et al. (2010) *Mol. Cell. Biol.* 30:1910-1922) and detected with Cy3-anti-rabbit [Jackson Immunoresearch]) as well as anti-acetylated and anti-gamma tubulins (mAbs 6-11B-1 and GTU88 respectively, co-detected with FITC anti-mouse [all Jackson Immunoresearch]) and imaged as described (Wen X. et al. (2010) *Mol. Cell. Biol.* 30:1910-1922). At least 200 cilia from three or more independent experiments were analyzed for robust Smo staining all along the cilium shaft (excluding those with weak signals or staining confined to the base).

Hh Pathway Gene Status.

Genomic DNA was isolated from tumors with the AllPrep DNA/RNA Mini Kit (Qiagen) and every exon from murine Smo, Sufu and Gli2 was PCR-amplified using a pair of nested primers containing M13 forward and reverse sequences. Excess primers and free nucleotides were removed with the ExoSAP-IT kit (USB) and PCR products were cycle-sequenced in both directions using M13 sequencing primers, a BigDye Terminator v3.1 Kit and a 3730×1 DNA analyzer (both Applied Biosystems). Sequence files were analyzed using Sequencher (GeneCodes) and Mutation Surveyor (SoftGenetics LLC) software.

Gene Copy Number Analyses.

Tumor DNA was labeled and hybridized to Mouse Genome 244K CGH Microarrays (Agilent) as per manufacturer recommended protocols, using normal diploid mouse genomic DNA as a reference. Data were normalized with Feature Extraction Software v9.5 (Agilent) and copy number variable regions were called in Nexus 4.0.1 (Biodiscovery) using a rank segmentation algorithm. An arbitrary threshold for copy number gains was set at log 2 ratio values of 0.6, with a minimum of 5 probes per segment. Copy number gains were confirmed by quantitative PCR (qPCR) on a MX3000P qPCR instrument (Stratagene) using 25 ng of genomic DNA/reaction. Target loci were compared to murine SINE1 elements and quantified on standard curves of normal diploid mouse DNA as described (Zhao X. et al. (2004) *Cancer Res.* 64:3060-3071) using the following primers:

```
Gli2 F:    5'-GCAGGACATTCCACACAGTTCTTG-3',    (SEQ ID NO: 4)

Gli2 R:    5'-ATAGGTGCTGGGATACAGGCTTG-3',     (SEQ ID NO: 5)

Ccnd1 F:   5'-TACCCTGACACCAATCTCCTCAACG-3',   (SEQ ID NO: 6)

Ccnd1 R:   5'-GGAATTCCCATCTTCCCAACTCC-3',    (SEQ ID NO: 7)

Sine1 F:   5'-AGATGGCTGAGTGGGTAAAGG-3'       (SEQ ID NO: 8)
and

Sine1 R:   5'-GTGGAGGTCAGAGGACAAACTT-3'.     (SEQ ID NO: 9)
```

Immunoblotting.

Frozen tumor samples were lysed in M-PER Mammalian Protein Extraction Reagent (Pierce) containing protease and phosphatase inhibitors. Lysates were separated on 4-12% Bis-Tris gels and proteins were transferred onto PVDF membranes with an iBlot (Invitrogen). Blots were blocked and incubated overnight at 4° C. with 5% milk containing one of the following primary antibodies; anti-cyclin D1 (Cell Signaling, #2922), anti-phospho(Ser473)-AKT (Cell Signaling, #4060), anti-total AKT (Cell Signaling #9272), anti-Gli2 (Cho A. et al. (2008) *Dev. Biol.* 321:27-39), or anti-actin (Santa Cruz Biotechnology, sc-47778), followed by a 1 h incubation at RT with appropriate HRP-conjugated secondary antibodies. Antigen-antibody interactions were visualized with SuperSignal West Dura Extended Duration Substrate (Pierce).

Example 1

Analysis of D473H Mutation.

Figure 1:
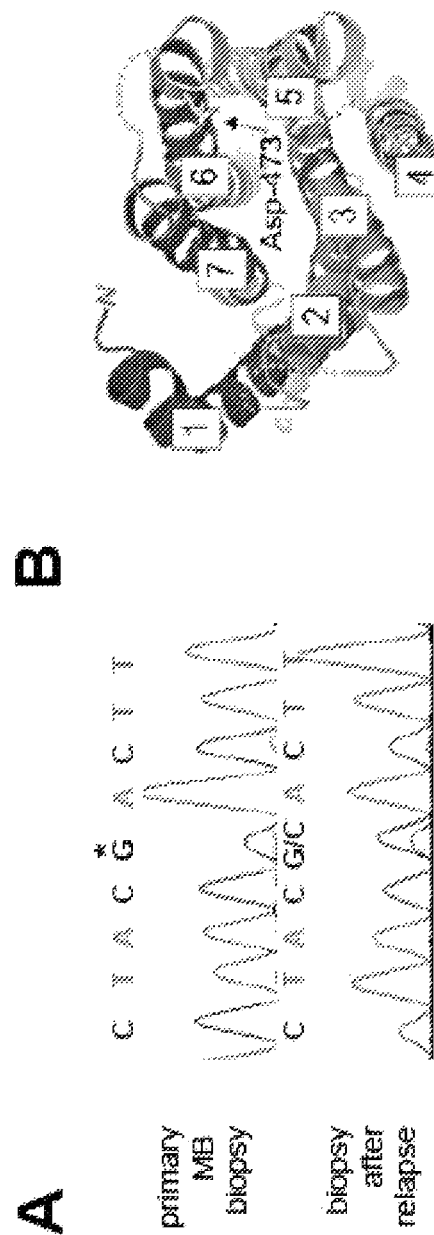
FIG. 1 shows identification of a SMO mutation in tumor samples from a medulloblastoma patient who relapsed after an initial response to GDC-0449. (A) Nucleotide sequence tracings showing a heterozygous mutation in SMO causing a Asp>His change at amino acid 473 (asterisk). This mutation was present in a metastatic biopsy taken at relapse, but was not present in the primary tumor prior to GDC-0449 treatment. (B) The GPCR architecture of SMO maps the location of the D473H mutation to the C-terminal end of TM6. Looking down at the extracellular face of the GPCR helix bundle (color-ramped from TM1 to TM7, with ectoloops left out for clarity), a molecular model of SMO built upon the rhodopsin (PDB: 2Z73) and β1-adrenergic receptor template (PDB: 2VT4) with MODELLER (Sali, A. and T. L. Blundell (1993) J. Mol. Biol. 234:779) shows the position of the Asp-473 residue facing the central binding cavity.
Figure 7:
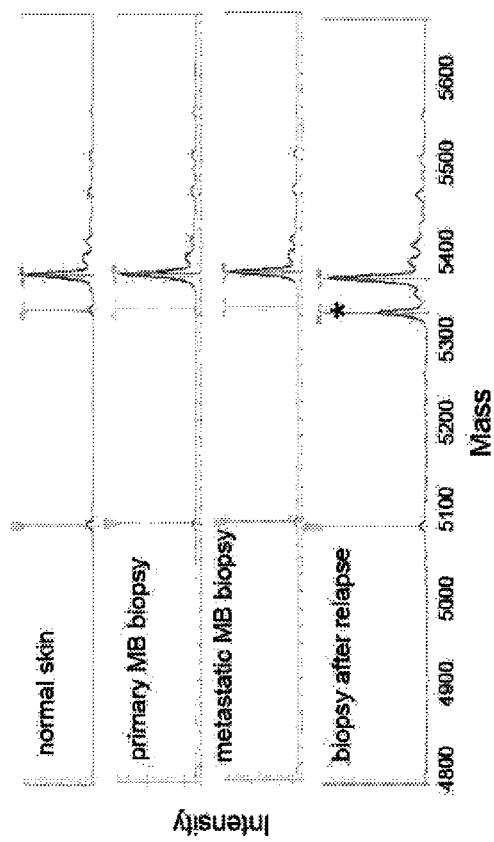
FIG. 7 shows mass spectra of extended DNA products for SMO WT and the D473H variant (asterisk) from multiple biopsies. The primary and metastatic medulloblastoma (MB) biopsies were both taken prior to GDC-0449 treatment. Mass spectra intensities represent arbitrary units.

We did not detect amplification of the SMO locus in the medulloblastoma patient's specimen (FIG. 6), but identified a heterozygous G to C missense mutation at position 1417, which is predicted to change codon 473 from Asp to His (D473H) (FIG. 1A). This change was not detected in the primary disease specimen. Using mass-spectrometry-based genotyping, we detected the mutant allele only in the biopsy taken after relapse, but not in normal skin from this individual or in the primary and metastatic disease biopsies taken prior to GDC-0449 treatment (FIG. 7). By deep sequencing, the mutant allele was not detected at an allele frequency of ≥0.1% in either the primary or metastatic disease biopsy obtained prior to GDC-0449 treatment. The mutant allele was also not detected by mass-spectrometry-based genotyping of 64 banked medulloblastoma specimens.

Figure 2:
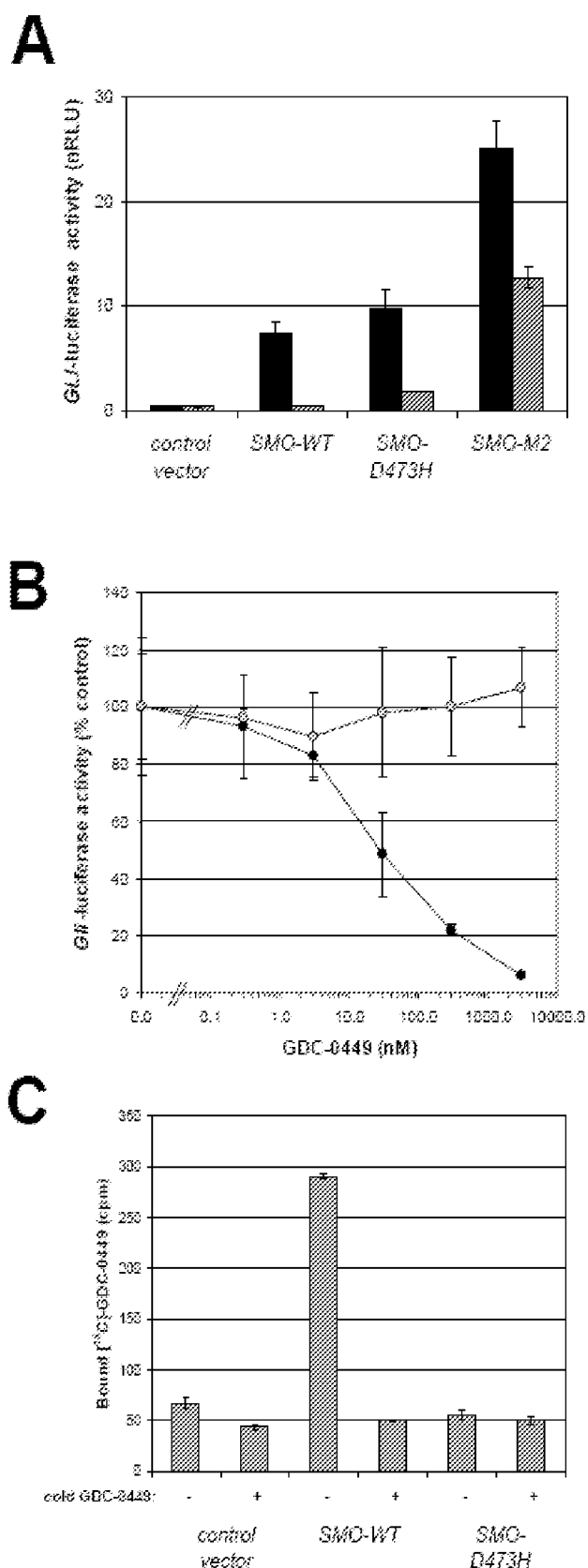
FIG. 2 shows The SMO D473H mutation confers resistance to the Hh pathway inhibitor GDC-0449. (A) GLI-luciferase reporter activity after transfection of SMO variants in the presence (grey bars) or absence (black bars) of PTCH1 DNA (20 ng). SMO-M2 represents a previously identified activating mutation. (B) GLI-luciferase reporter activity in C3H10T1/2 cells transfected with SMO-WT (closed circles) or SMO-D473H (open circles) after treatment with various doses of GDC-0449. Reporter activity is normalized to untreated cultures. (C) Binding of 14C-labeled GDC-0449 (5 nM) to HEK-293 cells transfected with SMO variants in the presence or absence of cold GDC-0449 (5 μM), to demonstrate specificity. Data in all experiments represent mean+/−SD.
Figure 8:
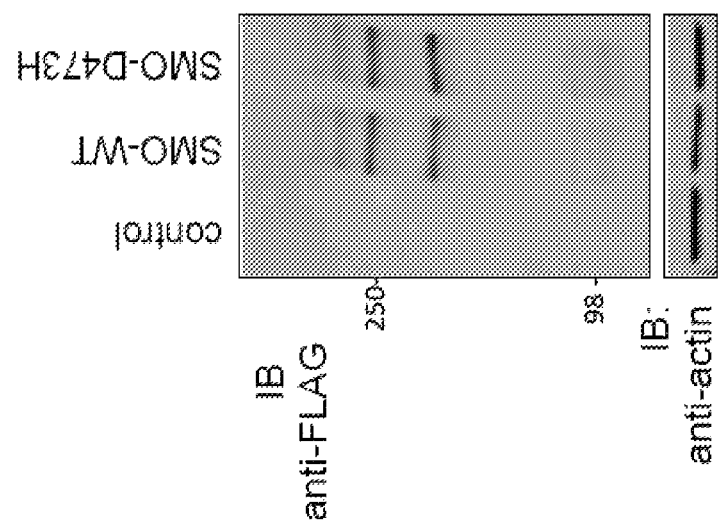
FIG. 8 shows immunoblot analysis of FLAG-tagged, SMO-WT and SMO-D473H transfected C3H10T1/2 cells probed with anti-FLAG or anti-actin as a loading control.
Figure 9:
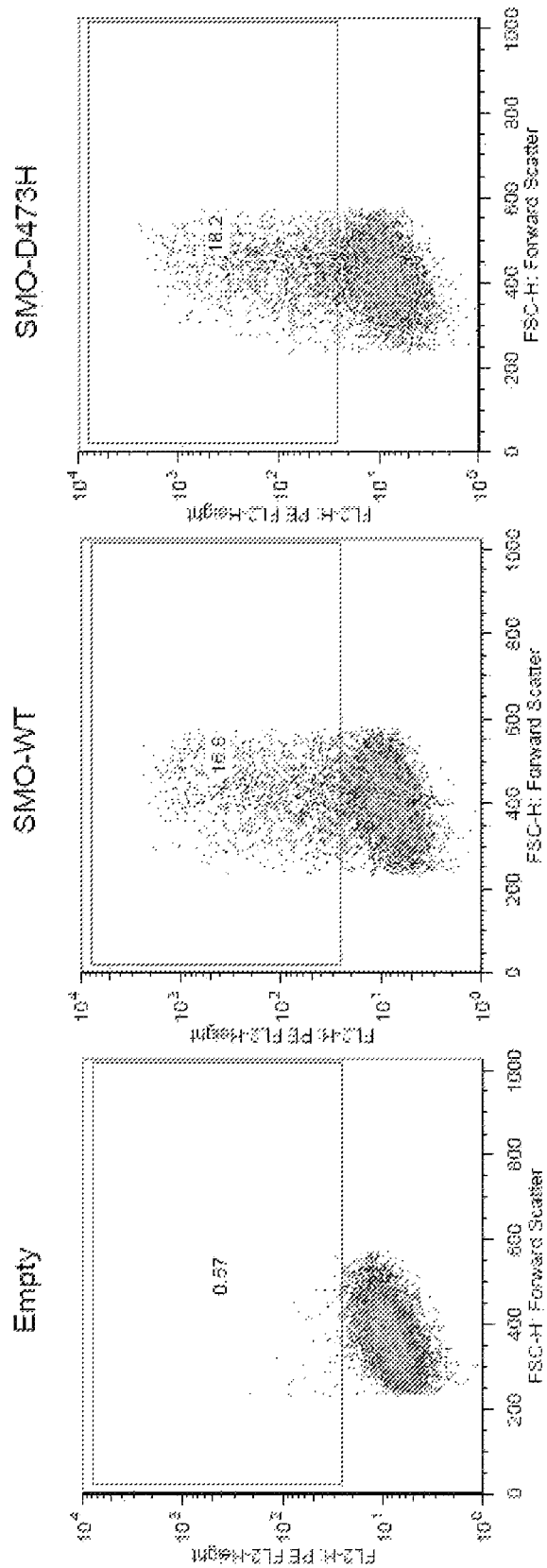
FIG. 9 shows flow cytometry analysis of FLAG-tagged, SMO-WT and SMO-D473H transfected C3H10T1/2 cells.
Figure 10:
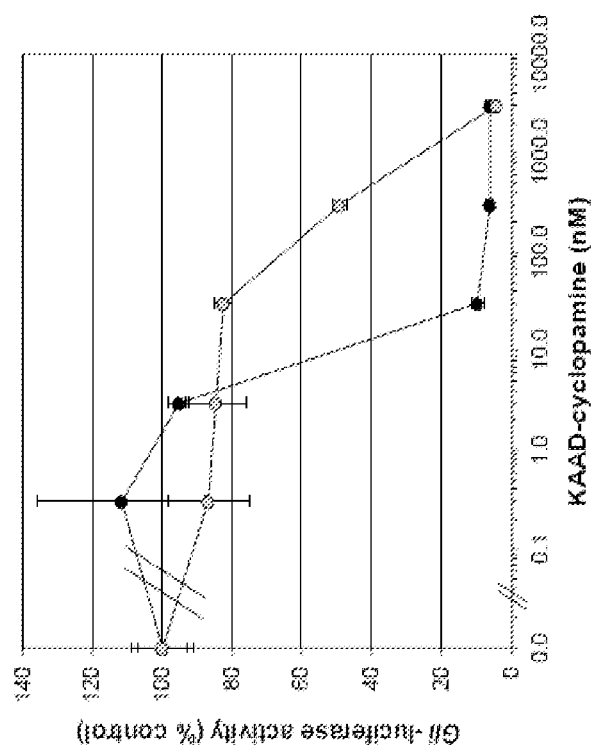
FIG. 10 shows SMO-D473H impairs the ability of KAAD-cyclopamine to suppress Hh signaling. GLI-luciferase reporter activity in C3H10T1/2 cells transfected with SMO-WT (closed circles) or SMO-D473H (open circles) after treatment with various doses of KAAD-cyclopamine.

To study the functional consequences of this mutation, we co-transfected C3H10T½ cells with expression vectors encoding SMO-WT or SMO-D473H together with a Hh-responsive GLI-luciferase reporter construct. SMO-WT and SMO-D473H were expressed at similar levels as determined by Western blotting (FIG. 8) and FACS analysis (FIG. 9). SMO-D473H transfection induced Hh pathway activity to levels comparable to that seen with SMO-WT, demonstrating that SMO-D473H is fully capable of activating Hh signaling (FIG. 2A). However, in contrast to the constitutively-active mutant SMO-M2 (J. Xie et al. (1998) *Nature* 391:90), the activity of SMO-D473H was not significantly higher than SMO-WT, and demonstrated a similar sensitivity as SMO-WT to PTCH1 inhibition, suggesting that SMO-D473H may not have inherent oncogenic potential and will only activate Hh signaling in the absence of PTCH1. To determine whether this mutation impedes the ability of GDC-0449 to inhibit Hh signaling, the half maximal concentration ($IC_{50}$) of drug required to inhibit GLI-luciferase reporter activity was measured (FIG. 2B). Although GDC-0449 inhibited reporter activity at an $IC_{50}$ of 20 nM in SMO-WT transfected cells, no inhibition was observed in SMO-D473H transfected cells even at concentrations as high as 3 µM; indicating that this mutation confers resistance to GDC-0449 without affecting its ability to transmit the Hh signal. SMO-D473H also impaired the ability of a chemically divergent SMO inhibitor, KAAD-cyclopamine (J. Taipale et al. (2000) *Nature* 406: 1005), to inhibit GLI-luciferase reporter activity with a 43-fold change in IC50 (FIG. 10).

Example 2

Functional Analysis of D473H Mutation.

In this study, we addressed whether the D473H mutation affected the receptor's ability to bind GDC-0449.

Whereas $^{14}$C-labeled GDC-0449 specifically bound to SMO-WT, it showed no specific binding to SMO-D473H (FIG. 2C). Thus, the inability of GDC-0449 to suppress Hh signaling in the context of the SMO-D473H mutation is associated with a deficiency in drug binding.

Figure 3:
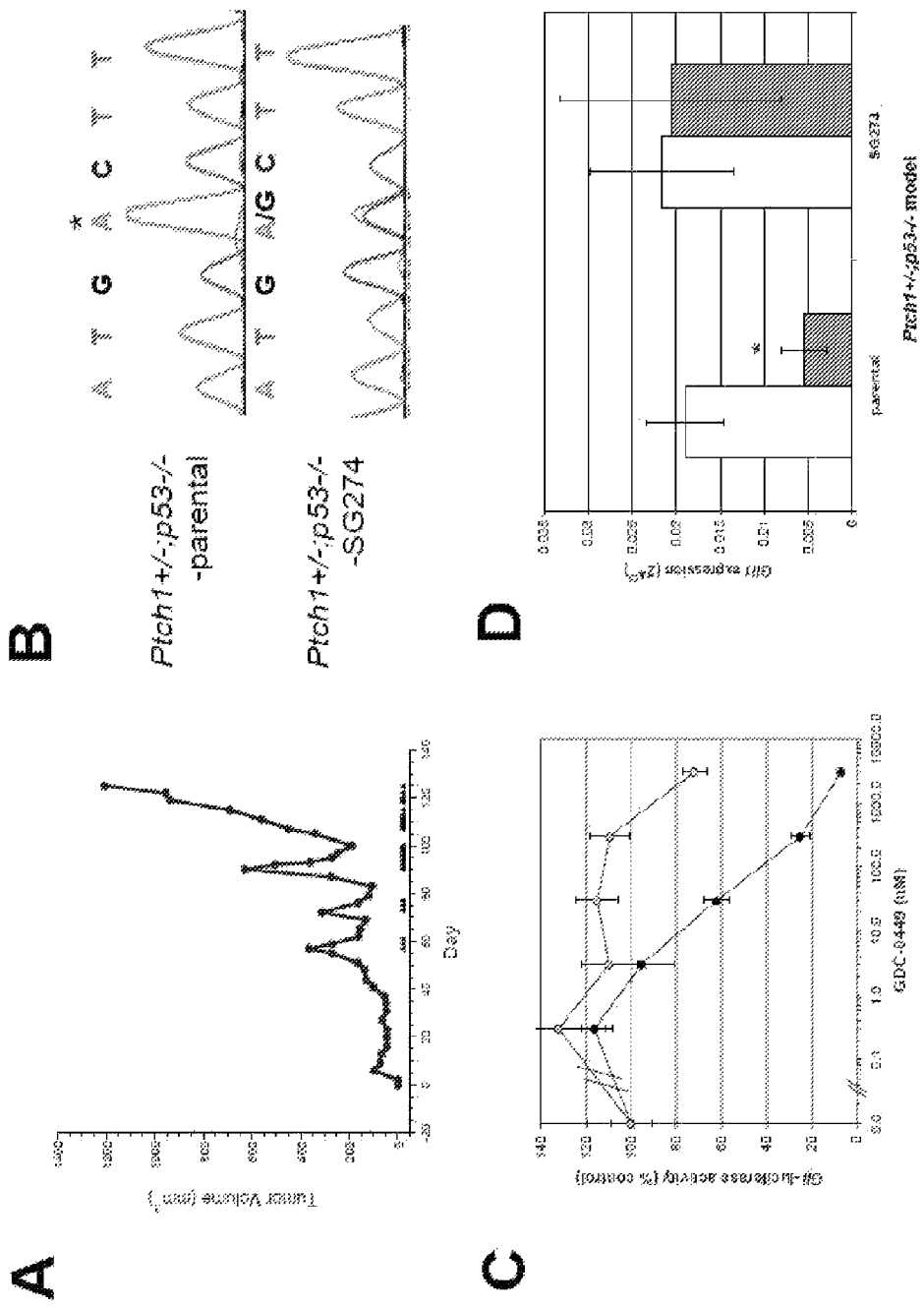
FIG. 3 shows acquired resistance to GDC-0449 through SMO mutation in a genetically-engineered mouse model of medulloblastoma. (A) Medulloblastoma allografts from Ptch+/−; p53−/− mice were made GDC-0449 resistant through intermittent daily dosing with 75 mg/kg GDC-0449. Treatment days are represented by triangles and tumors were excised once they failed to respond to twice daily dosing with GDC-0449. (B) Nucleotide sequence tracings from parental and a GDC-0449-resistant (SG274) medulloblastoma allografts showing a heterozygous mutation resulting in a D>G change at amino acid 477 of SMO (homologous to pos. 473 of human SMO). (C) GLI-luciferase reporter activity in C3H10T1/2 cells transfected with SMO-WT (closed circles) or SMO-D477G (open circles) after treatment with various doses of GDC-0449. (D) Quantitation of Gli1 mRNA levels by qRT-PCR from multiple (n=3) tumors collected 6 h after treatment with vehicle control (open bars) or 75 mg/kg GDC-0449 (closed bars) from parental and SG274 tumor-bearing mice. Data indicate mean+/−SD. *, p<0.05 (t test).
Figure 11:
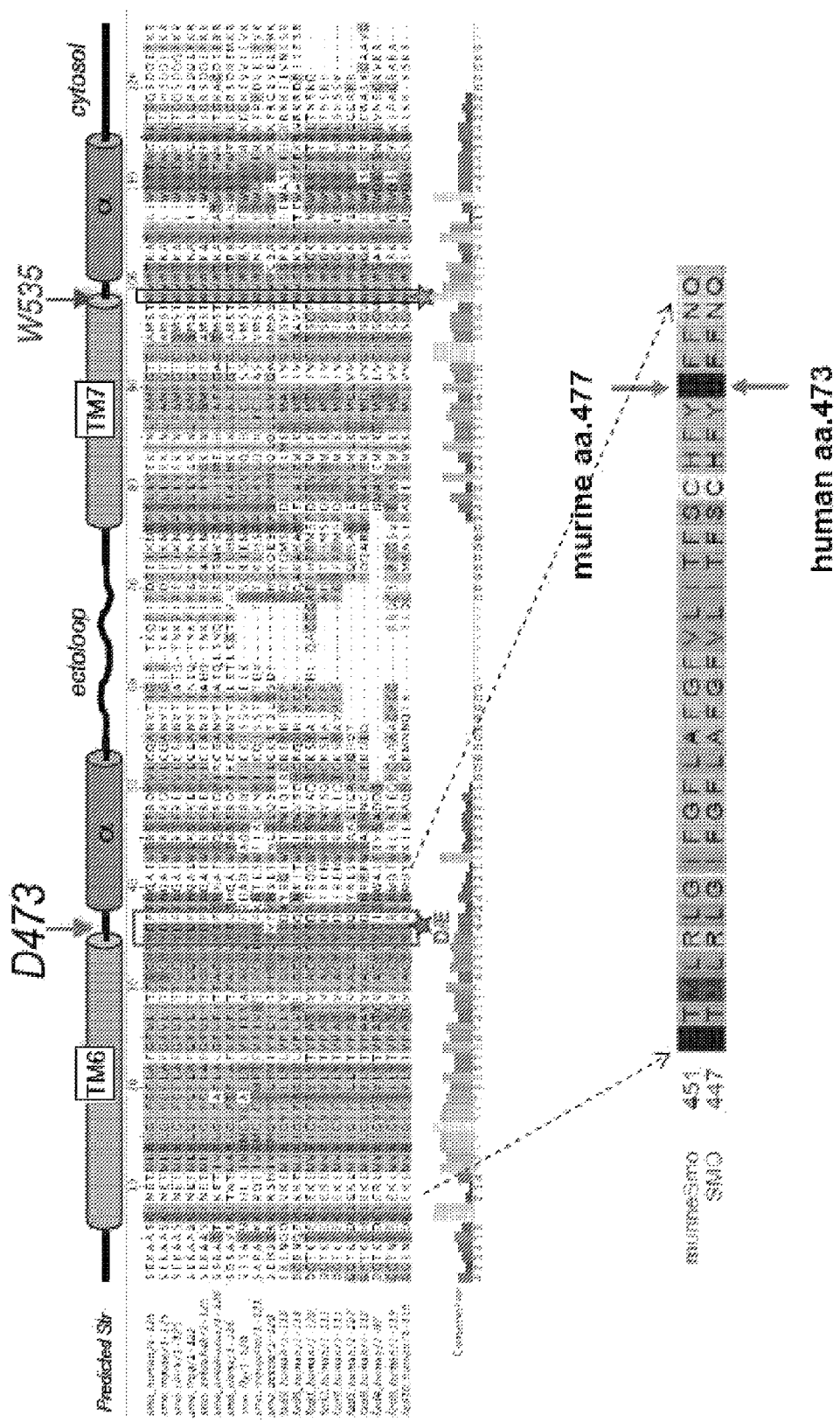
FIG. 11 shows the SMO Asp-473 residue is well conserved across SMO and Frzreceptors. An alignment across the TM6-TM7 region of representative SMO species variants and the ten human Frz receptor chains shows the conserved Asp/Glu residue at position 473. The TM7 tail position of Trp-535 that harbors the SMO-M2 activating mutation is also highlighted. Interestingly, both sensitive amino acid positions are closely followed by a short, membrane-associated amphipathic helix.

To further explore potential mechanisms of GDC-0449 resistance in medulloblastoma in vivo, we developed drug-resistant, subcutaneous allograft derivatives of medulloblastoma tumors from Ptch1+/−; p53−/− mice (J. T. Romer et al. (2004) *Cancer Cell* 6:229) through intermittent dosing until tumors no longer responded to twice daily dosing of GDC-0449. Using this approach we established 3 separate drug-resistant tumor lines, of which one model (SG274) is described here (FIG. 3A). Sequencing of Smo in the SG274 model revealed a heterozygous A to G missense mutation at position 1944, resulting in aspartic acid-477 to glycine (D477G) change, which was not identified in the parental, GDC-0449-sensitive, model (FIG. 3B). Strikingly, the corresponding residue in human SMO is the aspartic acid at position 473 that was mutated in the relapsed medulloblastoma patient (FIG. 11). GDC-0449 showed an ~100-fold decreased ability in suppressing Hh signaling in cells ectopically expressing the glycine variant at this position compared to WT (FIG. 3C).

Furthermore, GDC-0449 did not suppress Hh signaling in vivo, as demonstrated by the inability of GDC-0449 to downregulate Gli1 levels in SG274 tumors subcutaneously implanted in mice (FIG. 3D). Data from this mouse model thus provide additional evidence that mutation of SMO at this specific aspartic acid residue can confer resistance to GDC-0449. Additional mechanisms of resistance to GDC-0449 exist, as Smo mutations were not identified in the other 2 models.

Figure 12:
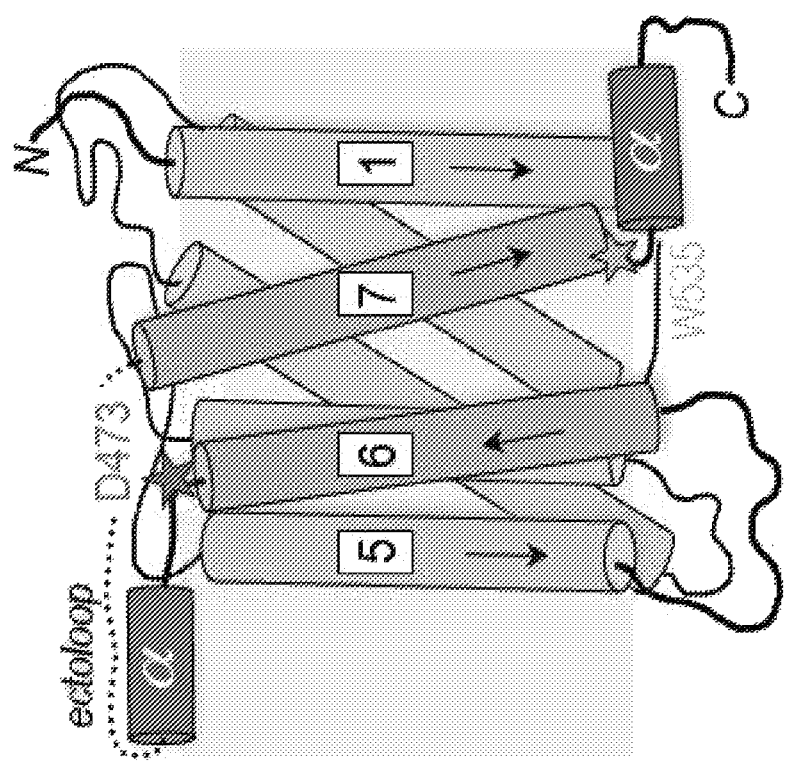
FIG. 12 shows the SMO Asp-473 residue is well conserved across SMO and Frz receptors. The GPCR fold of SMO maps the location of the D473H mutation to the C-terminal end of TM6, at the extracellular membrane interface. The SMO topology schematic shows the mirror image, cytosolic membrane interface location of the TM7 C-terminus W535L SMO-M2 activating mutation (Xie, J. et al. (1998) Nature 391:90). Both TM6 and TM7 are predicted to be followed by short amphipathic, membrane-associated helices.

Topology prediction and structural modeling of SMO map the Asp-473 residue to the C-terminal end of the sixth transmembrane segment (TM6), a position that is highly conserved across SMO orthologs and the related Frizzled family of Wnt receptors (FIG. 1B, FIG. 12). The heptahelical structure of SMO is required for binding of cyclopamine (J. Chen K. et al. (2002) Genes Dev. 16:2743) and is the target for ortho- and allosteric GPCR modulators (Goudet et al. (2004) Drug Discovery Today Therapeutic Strategies 1:125). Since Asp-473 is positioned at the extracellular lip of the central cavity formed by the canonical GPCR architecture (Rosenbaum, D. M. et al. (2009) Nature 459:356) of SMO, the nonconservative mutation of this residue may potentially destabilize the packing of SMO ectoloops or the inner topography of the protected binding pocket.

Our study shows that GPCR-like proteins can become drug resistant through the acquisition of genetic mutations. These findings have direct implications for the clinical development of SMO inhibitors in tumors where the Hh pathway is mutated, and may be applicable to future GPCR targets in cancer as many have been shown to play a critical role in tumor growth and metastasis (R. T. Dorsam and J. S. Gutkind (2007) Nat. Rev. Cancer 7:79). Furthermore, the demonstration that these mutations do not impact Hh signaling continues to support the rationale for targeting this pathway, but also highlighted the need to either identify second-generation SMO inhibitors capable of overcoming acquired resistance, identify inhibitors targeting downstream signaling molecules (J. M. Hyman et al. (2009) Proc. Natl. Acad. Sci. USA 106 (33):14132-14137), or potentially initiate earlier treatment, prior to therapy with radiation or other DNA damaging agents.

Example 3

D473 is Important for SMO Activity and Inhibition by GDC-0449.

Figure 13:
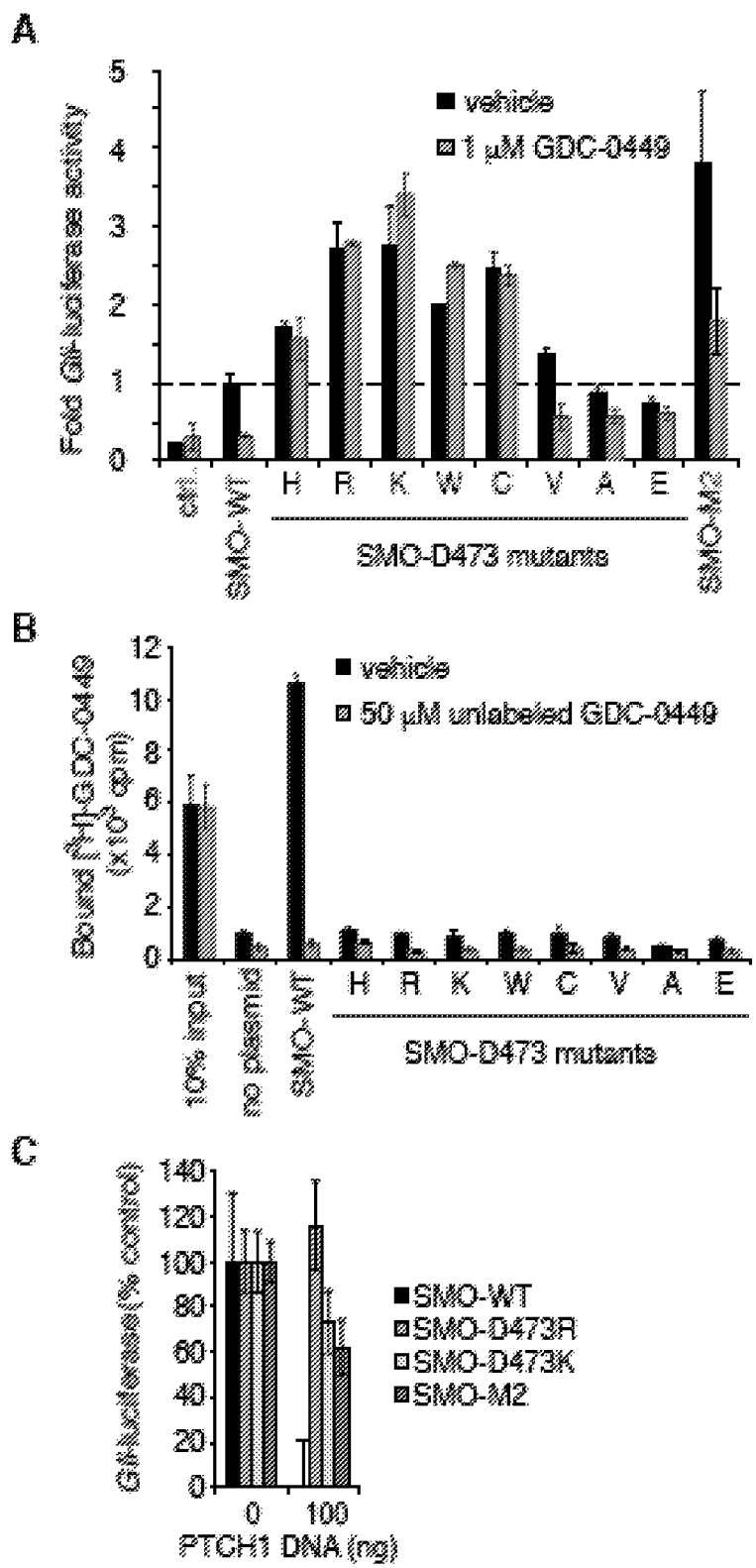
FIG. 13 shows that D473 is a key residue for SMO activity and GDC-0449 binding. (A) Gli luciferase activity in CH310T1/2 cells transfected with wild type or mutant SMO constructs. Reporter assays were performed in the presence (grey bars) or absence (black bars) of 1 μM GDC-0449 and values were normalized to those of SMO-WT. The activity level of SMO-WT in the absence of drug is indicated with a dotted (- - -) line across the graph to facilitate comparison. SMO-M2 is a previously described oncogenic mutant with a W535L substitution (Xie, J. et al. (1998) Nature 391:90). (B) binding of $^{3}$H-labeled GDC-0449 to HEK-293 cells transfected with various SMO plasmids in the presence (grey bars) or absence (black bars) of excess unlabeled GDC-0449. Drug binding was measured in counts per minute (cpm). (C) Gli-luciferase activity in CH310T1/2 cells co-transfected with PTCH1 and select SMO constructs. Values were normalized to maximum activity levels of cultures without PTCH1. Data in all experiments are means±SDs.

To better characterize the role of D473 in SMO function, we substituted this residue with every amino acid and analyzed the resulting mutants in a Gli-luciferase reporter assay in the presence or absence of 1 µM GDC-0449 (FIG. 13A; FIG. 18A). Apart from the possibly misfolded SMO-D473P, all mutants induced Hh pathway activity and were less sensitive to GDC-0449 inhibition than SMO-WT. The seemingly responsive D473V mutant was partially drug-resistant in a dose response assay (FIG. 18B). Surprisingly, the SMO-D473E mutant was also resistant to GDC-0449, even though this conservative substitution maintains a negative charge at this position. We next confirmed cell surface expression for several of these mutants (FIG. 18C) and tested their ability to bind GDC-0449 (FIG. 13B). Similar to SMO-D473H, resistance to this HPI correlated with a lack of SMO binding.

This assay is sensitive to even small changes in drug affinity of SMO, which may explain why the SMO-D473V mutant appears to be deficient in GDC-0449 binding but can still be inhibited at high drug concentrations. Collectively, these observations strongly suggest that D473 is critical for SMO inhibition by GDC-0449.

D473 could either be directly involved in GDC-0449 binding or could simply be required to maintain the correct SMO conformation for binding. Several mutants, including those with a positive charge such as D473K and D473R, were more active than SMO-WT and almost as active as the oncogenic SMO-M2 mutant (FIG. 13A; J. Xie et al. (1998) Nature 391:90), implying that D473 could be a structurally important residue. Consistent with this notion, the SMO-D473K and SMO-D473R mutants have auto-activating properties and are resistant to inhibition by PTCH1 (FIG. 13C). However, it is unlikely that they will be naturally occurring oncogenic or drug-resistant mutants, since these amino acid substitutions require two nucleotide changes.

Example 4

A screen of Chemically Diverse HPIs Identified Several SMO-D473H Antagonists.

Figure 14:
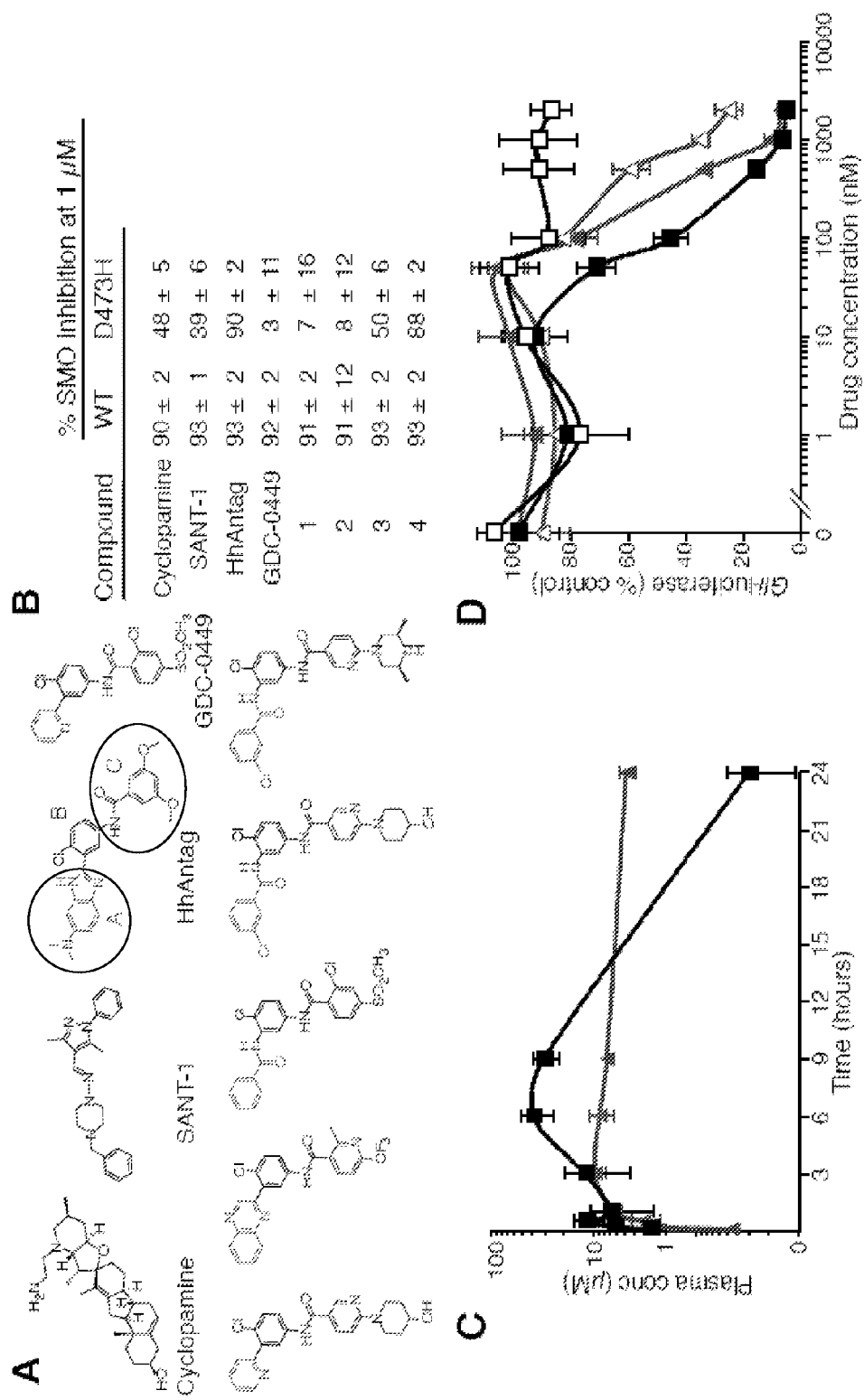
FIG. 14 shows that Compound 5 (Formula III) is a potent SMO-D473H antagonist with good pharmacokinetic properties in mice. (A) chemical structures of various SMO antagonists used in this study. A circle marks the A-ring, a second circle marks the C-ring and the B-ring is shown between the two for HhAntag. The other compounds contain variations of these structural elements. (B) compounds screened at 1 μM with % inhibition values of Gli-luciferase activity induced by SMO-WT or SMO-D473H overexpression in C3H10T1/2 cells. (C) mean plasma concentration versus time following a single oral 100 mg kg-1 dose of either compound 4 (black square) or compound 5 (grey triangle) in mice (n=24; three animals per time point). The structurally similar, but more potent compound 4 is cleared much more rapidly from the blood stream than compound 5 (t1/2 of 21/2 vs. 22 hours). (D) Gli-luciferase reporter activity of C3H10T1/2 cells transfected with SMO-WT (solid) or SMO-D473H (open) following a dose response of either GDC-0449 (black squares) or compound 5 (grey triangles). Reporter activity was normalized relative to a control reporter and to maximum activity levels. Compound 5 is less potent against SMO-WT than GDC-0449, but can inhibit the drug-resistant mutant. Data in (B) to (D) are means±SDs.

To identify SMO mutant inhibitors as potential therapeutics for GDC-0449 resistant tumors, we screened a panel of 53 antagonists (representative compounds are shown in FIG. 14A) with potent activity against the wild type protein (FIG. 14B). These compounds were either identified in high-throughput screens (both in house and by others) or were generated by hit-to-lead optimization of screening hits using traditional medicinal chemistry methods. C3H10T1/2 cells were co-transfected with wild type or mutant SMO expression vectors together with a Gli-luciferase reporter construct (Murone M. et al. (1999) Curr Biol. 9:76-84), and pathway activation was measured in the presence or absence of 1 µM compound. Interestingly, the benzimidazole HhAntag (Romer J. T. et al. (2004) Cancer Cell 6:229-240) was essentially equipotent against all SMO alleles despite several structural similarities with GDC-0449, indicating subtle differences in structure activity relationship (SAR) between these two compounds.

Various C-ring amide derivatives of GDC-0449 displayed weak potency against SMO D473H, as exemplified by compound I (refer to FIG. 14A for A-, B-, and C-ring nomenclature). By contrast, many C-ring amide derivatives of HhAntag retained potency (data not shown), demonstrating that the benzimidazole A-ring found in HhAntag is superior to the 2-pyridyl A-ring found in GDC-0449 at inhibiting this SMO mutant.

Looking at other A-ring substitutions, quinazolines (represented by compound 2) were found to be inactive, while the bis-amide compound 3 (Formula I) showed measurable activity despite having an identical C-ring to GDC-0449. This general class of bis-amides showed improved potencies against SMO-D473H once the optimal substitution pattern was found, exemplified by compounds 4 (Formula II) and 5 (Formula III).

Although the C-ring clearly contributes to inhibition of SMO-D473H, our SAR observations imply that A-ring substitutions can improve potency most dramatically. Specifically, an A-ring with both a hydrogen bond donor and acceptor, as found in the benzimidazole HhAntag and the bis-amide compounds 3-5, is preferred when binding to SMO-D473H relative to a hydrogen bond acceptor alone. Furthermore, SMO-D473H is partially resistant to to the natural plant alkaloid cyclopamine and to the hyrazinoimine, SANT-1.

Although we routinely use HhAntag as a tool compound to block Hh signaling in mice, this inhibitor is rapidly metabolized by human hepatocytes and is therefore not suitable as a therapeutic agent (Stephen E. Gould, unpublished observation). As our objective was to identify a SMO antagonist that might be capable of overcoming acquired GDC-0449 resistance in the clinic, we focused our efforts on the bis-amide class of inhibitors. Only three out of fourteen drug candidates from this group exhibited good pharmacokinetic properties in mice (data not shown). Of these, we choose to further investigate for these studies compound 5 (Formula III), which harbors a terminal half-life (t1/2) of about 22 hours (FIG. 14C) and displayed the most robust activity against both wild type and SMO-D473H, inhibiting Gli-luciferase reporter activity with an IC50 of 300 nM and 700 nM, respectively (FIG. 14D). Note that these IC50 values are overestimates due to overexpression of SMO in this assay system; approximately 10-fold less compound is sufficient to inhibit endogenous SMO following stimulation by Hh ligand (data not shown).

Example 5

Compound 5 (Formula III) Inhibits Tumor Growth Mediated by GDC-0449 Resistant Smo.

Figure 15:
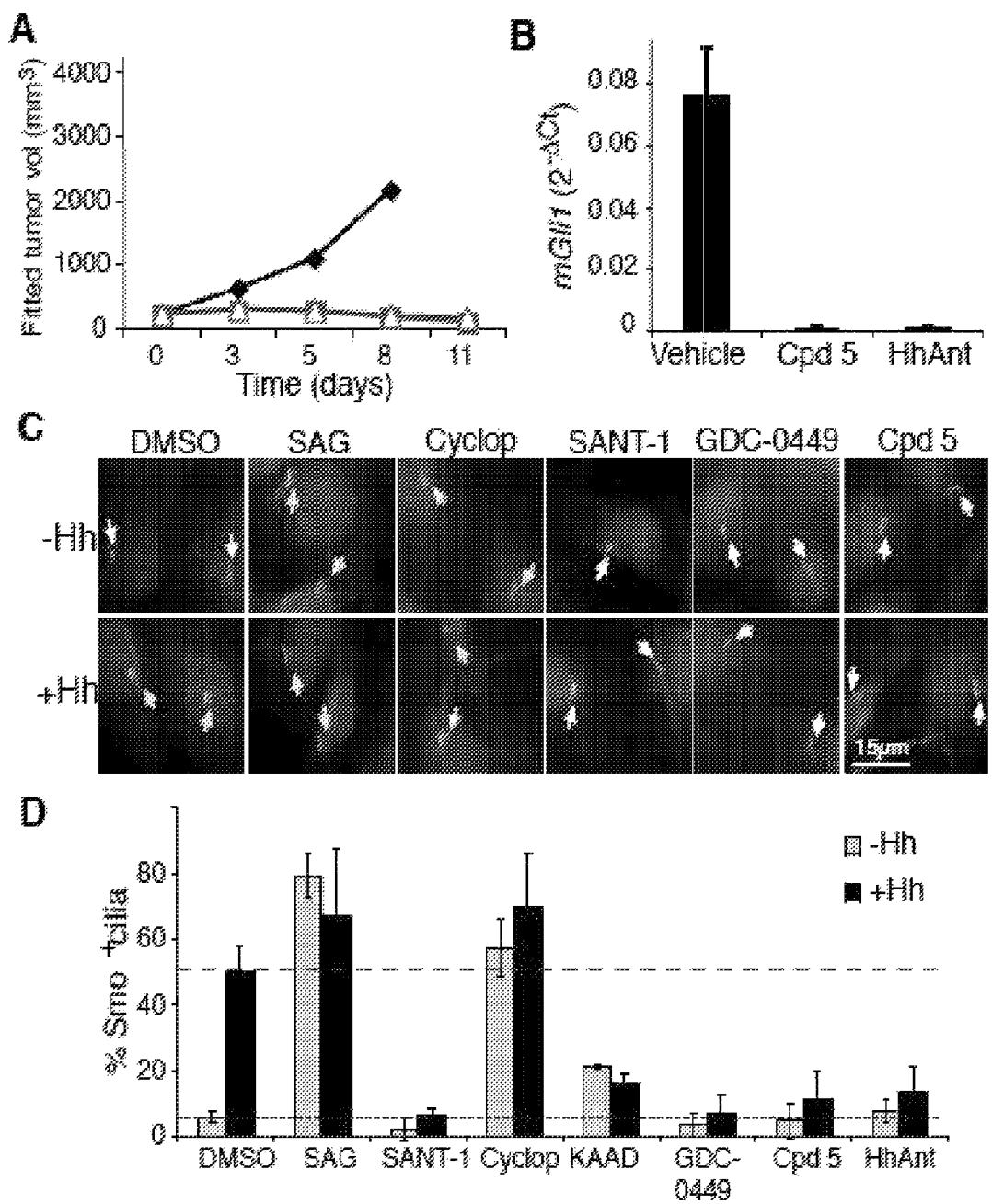
FIG. 15 shows that Compound 5 inhibits Smo-D477G dependent tumor growth and prevents ciliary accumulation of Smo in vitro. (A) fitted tumor volume of subcutaneous SG274 allografts treated orally with vehicle (n=4, black diamonds), 100 mg kg-1 compound 5 once daily (n=6, grey triangles) or 100 mg kg-1 HhAntag691 twice daily (n=6, grey squares).

It was important to determine whether compound 5 (Formula III) could also inhibit drug resistant Smo in vivo. To this extent, we generated mice with subcutaneous allografts of the murine Ptch$^{+/-}$; p53$^{-/-}$ MB tumor line SG274, which had been rendered resistant to GDC-0449 due to a D477G amino acid substitution in Smo, the same aspartic residue that was mutated in human SMO. These mice developed 125-350 mm$^3$ tumors within two weeks, after which oral drug treatment was initiated. Vehicle and GDC-0449 treated mice displayed unrestrained tumor growth and had to be euthanized after 9 days of treatment to prevent excessive tumor burden (FIG. 15A; data not shown). Strikingly, tumors in animals treated with compound 5 not only stopped growing but even started to shrink during this relatively short time. This tumor growth inhibition was accompanied by a downregulation in Gli1 mRNA levels (FIG. 15B), indicating that compound 5 can suppress Hh signaling mediated by GDC-0449 resistant Smo in vivo. Similar results were obtained with HhAntag.

Example 6

GDC-0449 and Compound 5 Both Interfere with Smo Translocation to the Primary Cilium.

Recently, several groups reported that diverse antagonists differentially affect the trafficking and localization of Smo to the primary cilium (Wilson C. W. et al. (2009) *PLoS One* 4:e5182; Wang Y. et al. (2009) *Proc. Natl. Acad. Sci. USA* 106:2623-2628; Rohatgi R. et al. (2009) *Proc. Natl. Acad. Sci. USA* 106:3196-201). Cyclopamine was found to promote ciliary accumulation of Smo in the absence of active Hh signaling, while other Smo inhibitors like SANT-1 instead prevented Shh and agonist-induced translocation of Smo to this organelle. Based on these and other observations Rohatgi and colleagues (Rohatgi R. et al. (2009) *Proc. Natl. Acad. Sci. USA* 106:3196-201) proposed a 2-step mechanism for Smo activation, in which full activation of this protein requires ciliary transport coupled to an as yet unidentified second activation step that allows Smo to engage the downstream signaling machinery in cilia. A key concept of their model is that Smo antagonists can be sub-divided in two classes; "SANT-1-like" inhibitors that influence trafficking of Smo to cilia and cyclopaminelike" inhibitors that affect the activation step. The authors further proposed that their model might be useful for overcoming drug resistance, anticipating complementary roles for these two classes of SMO antagonists in the clinic due to lack of cross-resistance. If this model were correct, then GDC-0449 and the SMO mutant inhibitors should differentially affect Smo trafficking to cilia.

To test this, we incubated confluent S12 cells (Frank-Kamenetsky M. et al. (2002) *J. Biol.* 1:10) with the indicated compounds for 16 hours in the absence or presence of Hh stimulation, and determined whether endogenous Smo co-localized with the primary cilium marker acetylated tubulin and/or the centrosomal marker γ tubulin (FIG. 15C and FIG. 15D). The control (DMSO treated) cells displayed very faint Smo staining in only a few cilia. As previously reported, stimulation with either Shh or the SMO agonist SAG (Chen J. K. et al. (2002) *Proc. Natl. Acad. Sci. USA* 99:14071-14076) resulted in robust translocation of Smo to the primary cilium, as did cyclopamine treatment. Like SANT-1, GDC-0449 did not promote ciliary enrichment and prevented Hh-induced Smo translocation.

Compound 5 (Formula III) and HhAntag had very similar effects on Smo localization, suggesting that their ability to inhibit mutant signaling does not involve Smo trafficking. This notion was further corroborated by the converse finding that KAAD-cyclopamine, a more potent version of cyclopamine (Taipale, J. et al. (2000) *Nature* 406:1005) that fully inhibits Smo-D473H at 1 μM, partially induced ciliary translocation in the absence of ligand (FIG. 19; FIG. 15D). All drugs were effective at preventing Hh pathway activation, as addition of Shh had no further effect on Smo trafficking Our data clearly demonstrates that inhibitors from the same class can in fact be used to overcome drug-resistance, as the SMO mutant inhibitors compound 5 and HhAntag affected Smo localization indistinguishably from GDC-0449. Furthermore, antagonists from different classes can display cross-resistance, since neither cyclopamine nor SANT-1 can fully inhibit Smo-D473H. Finally, subtle modifications of a compound, such as the addition of a lipid moiety to cyclopamine in the case of KAAD-cyclopamine, can dramatically affect both potency and the ability to influence Smo localization. Because cyclopamine and KAAD-cyclopamine likely bind the same site on Smo, their distinct effects on Smo trafficking could either be a consequence of inducing slightly different Smo conformations favoring one localization over another, or could be due to altered cell permeability allowing access of KAAD cyclopamine but not cyclopamine to pre-ciliary sites. In short, we found no obvious correlation between the ability of antagonists to manipulate Smo localization in a certain manner and their capacity to inhibit GDC-0449-resistant mutants.

Example 7

GDC-0449 has a Differential Effect on Gli1 mRNA Expression in two Additional Resistant MB Allograft Models.

In our three separate drug-resistant MB tumor lines created through intermittent dosing with GDC-0449, only SG274 was found to carry a mutation in Smo, indicating that additional mechanisms of resistance to GDC-0449 exist in models SG102 and SG152. Although mutations in the tumor suppressor SUFU predispose individuals to MB (Taylor M. D. et al. (2002) *Nat. Genet.* 31:306-310) and could in theory confer resistance to Smo antagonists, neither resistant MB allograft model was mutated in this gene. Naturally, resistance could also occur if these tumors had lost their dependence on Hh signaling. We therefore expanded the original resistant tumors and asked whether the Hh pathway was still active in these MB tumor lines and, if so, whether GDC-0449 could suppress signaling in vivo (FIG. 16A). Gli1 levels in vehicle treated, GDC-0449-resistant SG102 or SG152 allografts were comparable to those with control or Smo mutant SG274 allografts, indicating that the Hh pathway is similarly active in all models. Interestingly, GDC-0449 treatment down regulated Gli1 levels in control and SG102 tumors, but failed to impact Hh signaling in SG152 and SG274 tumors. These observations suggest that SG102 and SG152 possess distinct mechanisms of GDC-0449 resistance independent of Smo or Sufu mutations and, in the case of SG102, may entail an event downstream of Smo-dependent Gli1 regulation.

Example 8

Molecular Characterization of Two Additional MB Allograft Models Reveals Mechanisms of GDC-0449 Resistance Downstream of Smo.

To further investigate the mechanisms of GDC-0449 resistance, we used array Comparative Genomic Hybridization (aCGH) to identify gene copy number aberrations in the original tumors. Model SG102 contained an amplification of a region on chromosome 7 harboring the Hh target gene Ccnd1 (cyclin D1), while model SG152 had a high level focal amplification of a region on chromosome 1 encompassing the Hh pathway transcription factor Gli2 (FIG. 20). Both models contained additional copy number aberrations that previously have not been associated with either MB or abnormal Hh signaling (data not shown). Although cyclin D1 and Gli2 act downstream of Smo and have previously been implicated in the development of MB, we formally cannot rule out involvement of these other genomic alterations in GDC-0449 resistance. The Ccnd1 and Gli2 amplifications were independently confirmed by qPCR in SG102 and SG152 when compared to GDC-0449-sensitive control and Smo mutant SG274 tumors (FIG. 16B). These genomic alterations were maintained during subsequent propagation of the MB tumor lines, as expanded tumors exhibited enhanced mRNA expression and elevated protein levels of both cyclin D1 and Gli2 (FIG. 16B and FIG. 16C).

Cyclin D1 promotes proliferation through its ability to bind to and stimulate both CDK4 and CDK6, leading to phosphorylation of the retinoblastoma protein and entry into the cell cycle (Kim J. K. and J. A. Diehl (2009) *J. Cell. Physiol.* 220:292-296). Genetic ablation of Ccnd1 drastically reduces the incidence of MB in Ptch+/− mice (Pogoriler J. et al. (2006) *Development* 133:3929-3937), whereas enforced expression of cyclin D1 in Ink4c−/−, p53−/− GNPs enabled cells to initiate MBs when injected back into the brains of immunocompromised recipient animals (Zindy F. et al. (2007) *Cancer Res.* 67:2676-2684). GDC-0449 down regulated cyclin D1 levels in control tumors, consistent with Ccnd1 being an Hh target gene (FIG. 16D; Zindy F. et al. (2007) *Cancer Res.* 67:2676-2684). In contrast, cyclin D1 levels remained elevated in SG102 tumors, even though GDC-0449 diminished Gli1 mRNA levels. High cyclin D1 levels likely sustain tumor cell proliferation in the presence of GDC-0449, as Ccnd1 expression is no longer reliant on Hh signaling due to the gene amplification.

While GLI2 amplifications have been observed in human MB, they are relatively rare (Northcott P. A. et al. (2009) *Nat. Genet.* 41:465-472). Gli2 contains an amino-terminal repressor domain that when deleted results in a constitutively active protein with 30 times higher transcriptional activity (Roessler E. et al. (2005) *Hum. Mol. Genet.* 14:2181-2188). Tissue specific expression of this truncated transcription factor can lead to MB when ciliogenesis is impaired (Han Y. G. et al. (2009) *Nat. Med.* 15:1062-1065). Sequencing of Gli2 in model SG152 revealed no truncating mutations and both the full-length and repressor forms were detected by immunoblotting, indicating that Gli2 processing was relatively normal (FIG. 16C). Nevertheless, the oncogenic potential of Gli2 has been firmly established in a mouse model of BCC (Grachtchouk M. et al. (2000) *Nat. Genet.* 24:216-217) and viral mediated expression of the full-length protein allows GNPs to proliferate in vitro in the absence of Hh ligand (Oliver T. G. et al. (2003) *Proc. Natl. Acad. Sci. USA* 100:7331-7336). Similarly, enhanced Gli2 expression by means of gene amplification would obviously render the Hh pathway in tumor cells Smo-independent and therefore GDC-0449 insensitive.

Example 9

HPI Resistant MB Allografts are Sensitive to PI3K Inhibition.

Given the identification of resistance mechanisms downstream of SMO, we looked at other signaling pathways implicated in MB to see if targeting any of these might be an alternative therapeutic approach to combating GDC-0449 resistance. Abnormal phosphoinositide3-kinase (PI3K)/AKT signaling promotes tumor growth and survival of many human cancers, including MB (Vivanco I., and C. L. Sawyers (2002) *Nat. Rev. Cancer* 2:489-501; Vivanco I., and C. L. Sawyers (2002) *Nat. Rev. Cancer* 2:489-501). We therefore examined the level of activated AKT (phosphorylated at Ser473) and activated S6 (phosphorylated at Ser235/236) in our MB allograft models and were able to detect both phospho-proteins, suggesting that the PI3K/AKT pathway is active in these tumors (FIG. 17A). However, it is unlikely that increased PI3K/AKT signaling contributes to resistance, since AKT and S6 were also phosphorylated in GDC-0449-sensitive control tumors and an obvious PI3K gene-expression signature (Hartmann W. et al. (2005) *Clin. Cancer Res.* 12:3019-27; Saal L. H. et al. (2007) *Proc. Natl. Acad. Sci. USA* 104:7564-7569; Creighton C. J. (2007) *Oncogene* 26:4648-4655) was lacking in the micro-array profiles of the resistant models when compared to sensitive controls (data not shown). Importantly, the PI3K inhibitor GDC-0941 (Chang J. T. et al. (2009) *Mol. Cell.* 34:104-114) greatly reduced tumor growth in both control and resistant models, indicating that HPI-resistant tumors maintain their dependence on PI3K signaling (FIG. 17B). Tumor growth inhibition was accompanied by PI3K pathway modulation, as GDC-0941 treatment decreased pAKT and pS6 levels (FIG. 17A). Consequently, pharmacologic inhibition of PI3K/AKT signaling represents a promising therapeutic approach to treating HPI-resistant MB.

The foregoing Examples are for illustrative purposes only and should not be construed to limit the scope of the invention which is defined by the appended claims.

What is claimed is:

1. A method of
(a) detecting a mutant SMO protein in a sample comprising contacting protein from said sample with a monoclonal antibody that binds to a mutant SMO protein consisting of SEQ ID NO: 2 and having an amino acid other than aspartic acid at the amino acid position corresponding to amino acid 473 of SEQ ID NO: 2 with a higher affinity than to a wildtype SMO protein consisting of SEQ ID NO: 2 and having an aspartic acid at the amino acid position corresponding to amino acid 473 of SEQ ID NO: 2; or (b) identifying at least one SMO mutation in a sample comprising contacting nucleic acid from said sample with a nucleic acid probe that differentially binds a mutant SMO nucleic acid sequence as compared to a wildtype SMO nucleic acid sequence, wherein the wildtype SMO nucleic acid sequence encodes a SMO protein consisting of SEQ ID NO: 2 and having an aspartic acid at the amino acid position corresponding to amino acid 473 of SEQ ID NO: 2, and wherein the mutant SMO nucleic acid sequence encodes a mutant SMO protein consisting of SEQ ID NO: 2 and having an amino acid other than aspartic acid at the amino acid position corresponding to amino acid 473 of SEQ ID NO: 2.

2. The method of claim 1 wherein said probe in (b) is detectably labeled.

3. The method of claim 1 wherein said probe in (b) is an antisense oligomer.

4. The method of claim 1 wherein, in (b), the nucleic acid in said sample is amplified and contacted with said probe.

5. A method for identifying a tumor in a human subject that is resistant to treatment with GDC-0449 comprising
   (a) detecting a mutant SMO protein in a sample comprising contacting protein from said sample with a monoclonal antibody that binds to a mutant SMO protein consisting of SEQ ID NO: 2 and having an amino acid other than aspartic acid at the amino acid position corresponding to amino acid 473 of SEQ ID NO: 2 with a higher affinity than to a wildtype SMO protein consisting of SEQ ID NO: 2 and having an aspartic acid at the amino acid position corresponding to amino acid 473 of SEQ ID NO: 2; or
   (b) detecting a mutant SMO gene in a sample comprising contacting nucleic acid from said sample with a nucleic acid probe that differentially binds a mutant SMO nucleic acid sequence as compared to a wildtype SMO nucleic acid sequence, wherein the wildtype nucleic acid sequence encodes a SMO protein consisting of SEQ ID NO: 2 and having an aspartic acid at the amino acid position corresponding to amino acid 473 of SEQ ID NO: 2, and wherein the mutant nucleic acid sequence encodes a mutant SMO protein consisting of SEQ ID NO: 2 and having an amino acid other than aspartic acid at the amino acid position corresponding to amino acid 473 of SEQ ID NO: 2;
   whereby the presence of said mutant SMO gene or mutant SMO protein indicates that said tumor is resistant to treatment with a GDC-0449,
   wherein said method further comprises treating said subject having a tumor that is not susceptible to treatment with GDC-0449 with a compound that binds said mutant SMO protein.

6. The method of claim 5 wherein the presence or absence of said mutant SMO gene is determined by examining a nucleic acid sample.

7. The method of claim 5 wherein the presence or absence of said mutant SMO protein is determined by examining a protein sample.

8. The method of claim 1, wherein the method comprises contacting protein from said sample with a monoclonal antibody that binds to a mutant SMO protein consisting of SEQ ID NO: 2 and having an amino acid other than aspartic acid at the amino acid position corresponding to amino acid 473 of SEQ ID NO: 2 with a higher affinity than to a wildtype SMO protein consisting of SEQ ID NO: 2 and having an aspartic acid at the amino acid position corresponding to amino acid 473 of SEQ ID NO: 2.

9. The method of claim 1, wherein the method comprises identifying at least one SMO mutation in a sample comprising contacting nucleic acid from said sample with a nucleic acid probe that differentially binds a mutant SMO nucleic acid sequence as compared to a wildtype SMO nucleic acid sequence, wherein the wildtype nucleic acid sequence encodes a SMO protein consisting of SEQ ID NO: 2 and having an aspartic acid at the amino acid position corresponding to amino acid 473 of SEQ ID NO: 2, and wherein the mutant nucleic acid sequence encodes a mutant SMO protein consisting of SEQ ID NO: 2 and having an amino acid other than aspartic acid at the amino acid position corresponding to amino acid 473 of SEQ ID NO: 2.

10. The method of claim 5, wherein the method comprises contacting protein from said sample with a monoclonal antibody that binds to a mutant SMO protein consisting of SEQ ID NO: 2 and having an amino acid other than aspartic acid at the amino acid position corresponding to amino acid 473 of SEQ ID NO: 2 with a higher affinity than to a wildtype SMO protein having an aspartic acid at the amino acid position corresponding to amino acid 473 of SEQ ID NO: 2.

11. The method of claim 5, wherein the method comprises identifying at least one SMO mutation in a sample comprising contacting nucleic acid from said sample with a nucleic acid probe that differentially binds a mutant SMO nucleic acid sequence as compared to a wildtype SMO nucleic acid sequence, wherein the wildtype nucleic acid sequence encodes a SMO protein consisting of SEQ ID NO: 2 and having an aspartic acid at the amino acid position corresponding to amino acid 473 of SEQ ID NO: 2, and wherein the mutant nucleic acid sequence encodes a mutant SMO protein consisting of SEQ ID NO: 2 and having an amino acid other than aspartic acid at the amino acid position corresponding to amino acid 473 of SEQ ID NO: 2.

12. The method of claim 1, wherein the mutant SMO protein has a histidine (H), glycine (G), phenylalanine (F), tyrosine (Y), leucine (L), isoleucine (I), proline (P), serine (S), threonine (T), methionine (M), glutamine (Q), or asparagine (N) at the amino acid position corresponding to amino acid 473 of SEQ ID NO: 2.

13. The method of claim 5, wherein the mutant SMO protein has a histidine (H), glycine (G), phenylalanine (F), tyrosine (Y), leucine (L), isoleucine (I), proline (P), serine (S), threonine (T), methionine (M), glutamine (Q), or asparagine (N) at the amino acid position corresponding to amino acid 473 of SEQ ID NO: 2.

14. The method of claim 1, wherein the mutant SMO protein has a histidine (H) at the amino acid position corresponding to amino acid 473 of SEQ ID NO: 2.

15. The method of claim 5, wherein the mutant SMO protein has a histidine (H) at the amino acid position corresponding to amino acid 473 of SEQ ID NO: 2.

16. A method for treating a subject having a tumor comprising a SMO mutation, which tumor is not susceptible to treatment with GDC-0449, comprising:
   (a) detecting a mutant SMO gene in a sample comprising contacting nucleic acid from said sample with a nucleic acid probe that differentially binds a mutant SMO nucleic acid sequence as compared to a wildtype SMO nucleic acid sequence, wherein the wildtype nucleic acid sequence encodes a SMO protein consisting of SEQ ID NO: 2 and having an aspartic acid at the amino acid position corresponding to amino acid 473 of SEQ ID NO: 2, and wherein the mutant nucleic acid sequence encodes a mutant SMO protein consisting of SEQ ID NO: 2 and having an amino acid other than aspartic acid at the amino acid position corresponding to amino acid 473 of SEQ ID NO: 2; and
   (b) treating said subject with a compound that binds said mutant SMO protein.

* * * * *